(12) United States Patent
Li et al.

(10) Patent No.: US 12,312,625 B2
(45) Date of Patent: May 27, 2025

(54) ENGINEERING STRAIN PRODUCING CORDYCEPIN AND ITS DERIVATIVE 3'-DEOXYINOSINE, ITS PREPARATION METHOD AND APPLICATION

(71) Applicant: DALIAN UNIVERSITY, Dalian (CN)

(72) Inventors: Qian Li, Dalian (CN); Huiping Tan, Dalian (CN); Baomin Feng, Dalian (CN); Xiuping Li, Dalian (CN); Liang Wang, Dalian (CN); Yanghao Cheng, Dalian (CN); Xiang Li, Dalian (CN); Dapeng Wei, Dalian (CN); Tuo Kan, Dalian (CN); Chenyang Li, Dalian (CN); Rongshuai Jiang, Dalian (CN)

(73) Assignee: DALIAN UNIVERSITY, Dalian (CN)

( * ) Notice: Subject to any disclaimer, the term of this patent is extended or adjusted under 35 U.S.C. 154(b) by 0 days.

(21) Appl. No.: 18/626,782

(22) Filed: Apr. 4, 2024

(65) Prior Publication Data
US 2024/0344099 A1    Oct. 17, 2024

Related U.S. Application Data

(63) Continuation of application No. PCT/CN2022/091830, filed on May 10, 2022.

(30) Foreign Application Priority Data

Apr. 29, 2022  (CN) .......................... 202210463738.6

(51) Int. Cl.
| | | |
|---|---|---|
| C12P 19/40 | (2006.01) | |
| C12N 9/02 | (2006.01) | |
| C12N 9/16 | (2006.01) | |
| C12N 15/81 | (2006.01) | |

(52) U.S. Cl.
CPC ............ C12P 19/40 (2013.01); C12N 9/0004 (2013.01); C12N 9/16 (2013.01); C12N 15/815 (2013.01)

(58) Field of Classification Search
CPC ......... C12P 19/40; C12N 9/0004; C12N 9/16; C12N 15/815; C12N 9/0006; C12N 2800/102; C12N 2800/22; Y02P 20/55
See application file for complete search history.

(56) References Cited

PUBLICATIONS

First Office Action issued in Chinese Patent Application No. 202210463738.6; mailed Jul. 6, 2023, 9 pgs.
Notice of Grant issued in Chinese Patent Application No. 202210463738.6; mailed Aug. 1, 2023, 3 pgs.
International Search Report issued in International Application No. PCT/CN2022/091830; mailed Jan. 16, 2023, 10 pgs.
Written Opinion issued in International Application No. PCT/CN2022/091830; mailed Jan. 16, 2023, 9 pgs.
Preservation Certificate; Preservation No. CCTCC M 2022505; Name of strain: Cordyceps militaris L5111; Collection Center: China Collection Center for Typical Cultures; Preservation address: No. 299 Bayi Road, Wuchang District, Wuhan City, Hubei Province; Preservation date: Apr. 27, 2022.

*Primary Examiner* — Iqbal H Chowdhury
(74) *Attorney, Agent, or Firm* — HAUPTMAN HAM, LLP

(57) ABSTRACT

The present invention relates to the field of genetic engineering and process engineering, and discloses an engineering strain producing cordycepin and its derivative 3'-deoxyinosine, its preparation method and application. The method includes: codon optimizing genes Cm1 and Cm2; gene amplification and fragment recovering; methanol-induced promoter and terminator fragments; and inserting the genes into an expression vector and then transferring to *Pichia pastoris* for screening to obtain the engineering strain of *Pichia pastoris* of the present invention. The engineering strain can be applied to production of cordycepin and its derivative. The engineering strain prepared by the preparation method of the present invention has great advantages in producing cordycepin and its derivative. Due to the use of unique strains of *Cordyceps militaris* which have unique Cm1 and Cm2 genes, the efficiency of cordycepin production is greatly improved, and subsequently the green process of producing cordycepin and its derivative 3'-deoxyinosine with carbon dioxide can be realized.

1 Claim, 11 Drawing Sheets

Specification includes a Sequence Listing.

ENGINEERING STRAIN PRODUCING CORDYCEPIN AND ITS DERIVATIVE 3'-DEOXYINOSINE, ITS PREPARATION METHOD AND APPLICATION

RELATED APPLICATIONS

The present application is a Continuation of International Application Number PCT/CN2022/091830 filed May 10, 2022, which claims priority to Chinese Application Number 202210463738.6 filed Apr. 29, 2022, the disclosure of which are hereby incorporated by reference herein in their entireties.

INCORPORATION BY REFERENCE

The sequence listing provided in the file entitled C5998-034_Sequence_Listing.xml, which is an ASCII text file that was created on Apr. 2, 2024, and which comprises 20,690 bytes, is hereby incorporated by reference in its entirety.

FIELD OF THE INVENTION

The present invention relates to the field of genetic engineering and process engineering, and in particular, to an engineering strain producing cordycepin and its derivative 3'-deoxyinosine, its preparation method and application.

BACKGROUND

Cordycepin is a main active component of medicinal fungi, *Cordyceps militaris*, and has natural biological activity and unique pharmacological effects, including antibacterial, anti-inflammatory, anti-tumor, anti-leukemia effects, etc., and has great development value and broad market prospects in both medicine and health care. At present, cordycepin is mainly obtained through chemical synthesis, extraction from the fruiting body of *Cordyceps militaris* or mycelium fermentation. However, the cost of raw materials for chemical synthesis is high, and the synthesis route is complicated, and the yield is low. It has been reported by research institutes both at home and abroad that cordycepin can be obtained from the *Cordyceps militaris* fruiting body and mycelium fermentation, but disadvantages such as relatively long production cycle and low productivity, render a relatively high price of cordycepin. So far, there has been no report of industrial production of cordycepin.

With the development of omics technology, the biosynthesis pathway of cordycepin in *Cordyceps militaris* has been basically clarified. It has been reported that a cell factory for cordycepin synthesis has been successfully constructed using *Saccharomyces cerevisiae* as chassis cells. However, due to the factors such as low-level expression of exogenous genes, etc., the fermentation yield of cordycepin is relatively low. Therefore, there is an urgent need to develop a green and cost-effective process to produce cordycepin.

In recent years, unconventional yeasts such as *Pichia pastoris, Hansenia pastoris*, and *Kluyveromyces lactis* have attracted widespread attention due to their advantages such as wide substrate spectrums, high density culture and strong stress resistances. Some unconventional yeasts have been used in industry as new yeast expression systems to produce a variety of high value-added products, biofuels, and biomaterials. In addition, genomes of many unconventional yeasts have been fully sequenced, and gene editing tools have been developed to provide a strong technical guarantee for construction of unconventional yeast cell factories. However, there have been no reports on research of heterologous synthesis of cordycepin using unconventional yeast as chassis cell.

In addition, in *Cordyceps militaris*, cordycepin could be deaminized to produce 3'-deoxyinosine, which is considered to be a detoxification mechanism of cordycepin. Moreover, 3'-deoxyinosine can be used as a monomer to produce bio-based materials, especially since 3'-deoxyinosine contains rigid rings and multiple hydroxyl groups, and does not need the amino protection strategy to be considered when synthesizing polymers with a cordycepin monomer. Therefore, it has the potential to develop special engineering plastics, whose potential material characteristics are very likely to be far better than bio-based materials derived from aliphatic chains with good application prospects.

SUMMARY OF THE INVENTION

To overcome disadvantages of the prior art, the present invention provides an engineering strain producing cordycepin and its derivative 3'-deoxyinosine, its preparation method and application. The engineering strain is a self-flocculating strain of *Pichia pastoris*, which produces cordycepin and its derivatives with high titers and short production time during fermentation, and the composition of the fermentation medium is simple and is conducive to subsequent separation. Due to the self-flocculating characteristics of the *Pichia pastoris* used, the centrifugation step can be simplified. The flocculating strain can achieve in-situ fermentation-separation coupling through a simple solid-liquid separation device, to further improve productivity. In addition, flocculation can improve the density of the strain, further increasing the titer of a target product and shortening the fermentation time. Moreover, the production mode of cordycepin or 3'-deoxyinosine can be switched within the same strain through pH regulation.

The purpose of the present invention above is achieved through the following technical solution: a preparation method for an engineering strain producing cordycepin and its derivative 3'-deoxyinosine, including the following steps:

1. optimizing an oxidordeuctase gene Cm1 and a metal ion dependent phosphohydrolase gene Cm2 from *Cordyceps militaris* L5111 according to *Pichia pastoris* codon bias, a nucleotide sequence of Cm1 being shown in SEQ ID NO. 1, a nucleotide sequence of Cm2 being shown in SEQ ID NO. 2, the *Cordyceps militaris* L5111 being preserved at the China Center for Type Culture Collection, and the preservation address is No. 299, Bayi Road, Wuchang District, Wuhan, Hubei Province, with the preservation date of 27 Apr. 2022, the preservation number of CCTCC M 2022505, and the Latin name of *Cordyceps militaris*;
2. performing PCR amplification on the genes Cm1 and Cm2 described in step 1, and recovering fragments through agarose gel electrophoresis;
3. cloning methanol-induced promoters DAS2p, AOX1p, and FLD1p and terminators AOX1t, RPS25At, and CYCt fragments of *Pichia pastoris*; and
4. constructing an expression vector of *Pichia pastoris*, then linking the promoters DAS2p, AOX1p, and FLD1p, and the structural genes Cm1 and Cm2 as described in step 1, then transferring into *Pichia pastoris* through chemical or electrical performance, and screening to obtain an engineering strain of *Pichia pastoris* through a resistance marker carried by the expression vector, wherein a *Saccharomyces cerevisiae*

FLO1 gene (whose genetic system name is YAR050W) is introduced into the *Pichia pastoris* and the FLO1 on the genome is secondarily extended by gene editing.

Another purpose of the present invention is to protect an engineering strain producing cordycepin and its derivative 3'-deoxyinosine prepared by the preparation method above.

A further purpose of the present invention is to protect an application of the engineering strain producing cordycepin and its derivative 3'-deoxyinosine.

Furthermore, the application of the engineering strain producing cordycepin and its derivative 3'-deoxyinosine includes producing cordycepin and its derivative 3'-deoxyinosine.

Compared with the prior art, the present invention has the following beneficial effects: the Cm1 and Cm2 genes overexpressed by the engineering strain prepared by the preparation method of the present invention are derived from the high cordycepin-producing *C. militaris* L5111 isolated in our laboratory, and the Cm1 protein sequence has 14 amino acids different from the reported Cm1 protein sequence of *Cordyceps militaris*. The cordycepin yield of *C. militaris* L5111 is about 5 times higher than that of the reported strain. In terms of the expression host, the present invention selects an unconventional yeast, *Pichia pastoris*, which has great advantages in the production of cordycepin and its derivatives, specifically: (1) high titer and short production time: it has been reported that the yield of optimized *Saccharomyces cerevisiae* cordycepin expression system is only about 0.1 g/L, and the fermentation time is 3-7 d; and the yield of *Cordyceps militaris* cordycepin liquid fermentation system is 0.1-1.0 g/L, with the fermentation time at 30-40 d, while the fermentation time of *Pichia pastoris* only takes 7-8d, which can be shortened by more than ⅔ compared with *Cordyceps militaris*. The unoptimized shake flask system has reached a yield of nearly 1.0 g/L (the shake flask yield after optimization is close to 2.7 g/L), and the $OD_{600}$ is 8-12. The $OD_{600}$ of high-density culture of *Pichia pastoris* in a fermentation tank can reach about 100, and the yield for the coupled fermentation and separation system can reach 5-10 g/L. Therefore, the *Pichia pastoris* system has great advantages in both production titer and intensity for synthesizing cordycepin. (2) The simple composition of fermentation medium is beneficial to subsequent separation: *Cordyceps militaris*, a filamentous fungal system, has high requirements on the culture medium system. The culture medium has the complex composition, a large number of organic components, and complex metabolites, including a lot of extracellular polysaccharides and other substances that interfere with the subsequent separation of cordycepin. Moreover, on the one hand, *Pichia pastoris* can use cheap methanol as a carbon source, particularly considering the technology of converting carbon dioxide into one-carbon methanol is becoming increasingly mature, and a green process of using carbon dioxide to produce cordycepin and its derivatives can be realized in the future. On the other hand, *Pichia pastoris* can use FM22 or BSM mixed salt fermentation system, with ammonium salt as the nitrogen source, and the synthesized inorganic culture system will further reduce the complexity of the separation system. Moreover, it is found through determination that more than 95% of cordycepin and its derivatives are outside *Pichia pastoris* cell, which allows further application of the coupled fermentation-separation and other technologies. (3) The present invention only needs to adjust the initial pH of the fermentation and can use the same strain to complete the mode switch of producing cordycepin or its derivative 3'-deoxyinosine, and the extremely low content of the other product will not interfere with the separation. For example, when the pH is 4-6 and the cordycepin production mode is in place, HPLC can hardly detect a product peak of 3'-deoxyinosine. Similarly, when the pH is 7-8 and the 3'-deoxyinosine production mode is in place, the end point content of cordycepin is less than 1%.

BRIEF DESCRIPTION OF THE DRAWINGS

The following further describes the present invention with reference to the accompanying drawings and implementations.

Figure 1:
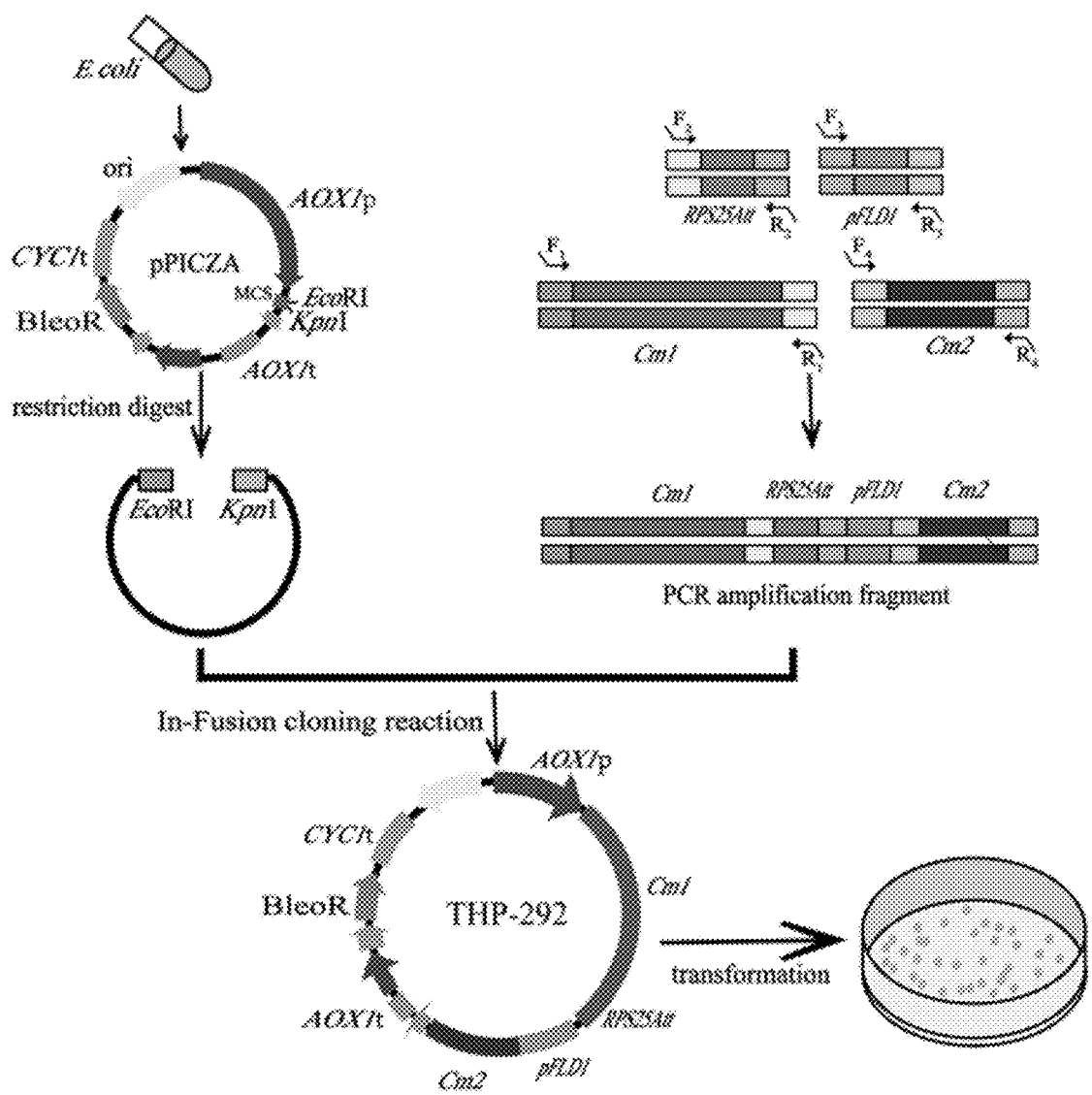
FIG. 1 is a flowchart of construction of an expression vector.

In the drawings: 1. refill bottle; 2. peristaltic pump A; 3. rotor flowmeter; 4. humidifier; 5. fermentation tank; 6. solid-liquid separator; 7. eluent; 8. peristaltic pump B; 9. changeover valve A; 10. adsorption separation column; 11.

collection bottle A; 12. changeover valve B; 13. peristaltic pump C; 14. collection bottle B.

DETAILED DESCRIPTION

The present invention is described in detail by specific embodiments below, but the scope of protection of the present invention is not limited. Unless otherwise specified, the experiment methods used in the present invention are all conventional methods, and the experimental instruments, materials and reagents used all can be obtained from commercial channels. The following *Cordyceps militaris* L5111 is preserved at the China Center for Type Culture Collection, and the preservation address is No. 299, Bayi Road, Wuchang District, Wuhan, Hubei Province, the preservation date is 27 Apr. 2022, the preservation number is CCTCC M 2022505, and the Latin name is *Cordyceps militaris*. The nucleotide sequence of Cm1 is described as SEQ ID NO. 1, and the nucleotide sequence of Cm2 is described as SEQ ID NO. 2.

Related Materials and Methods

I. Culture Medium and Reagents
YPD Medium (1 L):
  20 g glucose, 5 g peptone, 5 g yeast extract, and add 20 g agar to form the solid medium; YPDS (1 L):
  20 g glucose, 5 g peptone, 5 g yeast extract, 18 g Sorbitol, and add 20 g agar to form the solid medium; Low salt LB (1 L):
  10 g tryptone, 5 g yeast powder, 5 g NaCl, and add 20 g agar to form the solid medium, pH=7.0-7.2. 121° C., 15 min.
BMG Medium:
  (1.1) 10% glycerol: according to glycerol density, calculating 10 mL requires weighing 12.63 g glycerol, adding an appropriate amount of deionized water, finally adjusting the volume to 100 mL, and then disinfecting through filtration or autoclaved sterilization.
  (1.2) Phosphate (pH=6.0): weighing 3.01 g $K_2HPO_4$ ($3H_2O$) and 11.81 g $KH_2PO_4$, adding an appropriate amount of deionized water to dissolve, and finally adjusting the volume to 100 mL at 121° C. for 15 min.
  (1.3) 13.4% YNB: taking 3.4 g YNB powder without ammonium sulfate and 10 g ammonium sulfate powder, adding an appropriate amount of deionized water to dissolve, finally adjusting the volume to 100 mL, and sterilizing the solution by filtering through the 0.22 μm filter membrane.
  (1.4) 0.02% biotin: weighing 20 mg biotin, adding 100 mL deionized water to dissolve to prepare a mother liquor, taking 2 mL biotin, and sterilizing by filtering through the 0.22 μm filter membrane.
  Finally, all the solutions above are mixed, and 700 mL deionized water is added to adjust the volume to 1 L. If the host cell is *Pichia pastoris*, 2 mL (the concentration of 10 g/L) histidine should be added and stored at 4° C.
BMM Induction Medium:
  (2.1) Phosphate (pH=6.0): weighing 3.01 g $K_2HPO_4$ ($3H_2O$) and 11.81 g $KH_2PO_4(3H_2O)$, adding an appropriate amount of deionized water to dissolve, and finally adjusting the volume to 100 mL, autoclaved at 121° C. for 15 min.
  (2.2) 13.4% YNB: taking 3.4 g YNB powder without ammonium sulfate and 10 g ammonium sulfate powder, adding an appropriate amount of deionized water to dissolve, finally adjusting the volume to 100 mL, and sterilizing by filtering the solution through the 0.22 μm filter membrane.
  (2.3) 0.02% biotin: weighing 20 mg biotin, adding 100 mL deionized water to dissolve to prepare a mother liquor, taking 2 mL biotin, and sterilizing by filtering through the 0.22 μm filter membrane.
  Finally, all the solutions above are mixed, and 5 mL methanol and 700 ml deionized water are added to adjust the volume to 1L. If the host cell is *Pichia pastoris*, 2 mL histidine (at the concentration of 10 g/L) should be added and stored at 4° C.

II. Yeast Genome Extraction:
  (3.1) Take 1 mL overnight yeast culture to be centrifuged at 12000 rpm for 1 min and discard the supernatant; repeat this step.
  (3.2) Take 1 mL ultrapure water to suspend the slurry, and centrifuge at 12000 rpm for 1 min.
  (3.3) Suspend the slurry by adding 500 μL lysate, and further add 25 μL 5 mol/L NaCl.
  (3.4) Take ⅓-½ of solution volume of glass beads into a new 1.5 mL centrifugal tube, and pour the liquid mentioned above.
  (3.5) Shake for 7 min. Heat is produced during shaking, which would cause DNase renatured, thus the tube needs to be placed on ice during the process.
  (3.6) Centrifuge at 12000 rpm for 5 min and take the supernatant into a new centrifugal tube. Pay attention not to absorb the glass beads.
  (3.7) Add an equal volume of phenol:chloroform:isoamyl alcohol (25:24:1) mixed liquor to the liquid in step (3.6), vortex for 15s, and centrifuge at 12000 rpm for 10 min.
  (3.8) Take 200 μL of supernatant into a new centrifugal tube and add 2-2.5 times the volume of pre-cooled anhydrous ethanol.
  (3.9) Freeze at −80° C. for 1-4h, and then centrifuge at 12000 rpm for 5-10 min, and discard the supernatant, and there is a small amount of precipitate resides at the bottom of the centrifugal tube.
  (3.10) Add 1 mL 70% pre-cooled ethanol, vortex, and suspend the precipitate.
  (3.11) Centrifuge at 12000 rpm for 5 min and discard the supernatant.
  (3.12) Repeat steps (3.10) and (3.11).
  (3.13) Use a vacuum pump to drain residual liquid.
  (3.14) Place at room temperature for 30 min until the DNA precipitate becomes transparent, then add 50 μL of ultrapure water and 0.5 μL of RNase.
  (3.15) Store the genome solution at −20° C.

III. PCR Fragment Cloning
  The present invention uses high-fidelity enzymes for PCR amplification, and the amplification system is as follows:

| PCR system: | |
| --- | --- |
| Primer F/R: | 1 μL each |
| DNA template: | 1 μL |
| Primer STARMAX: | 10 μL |
| Ultrapure water: | 8 μL |
| Total: | 20 μL |

After the amplification is completed, all products are loaded for electrophoresis, and then the gel is recovered.

IV. In-Fusion Linking

| Linking system: (the molar ratio of small fragment:large fragment is 2:1) | |
| --- | --- |
| Small fragment (PCR product): | 1 μL |
| Large fragment (enzyme-digested product): | x μL |
| 5x In-Fusion HD Enzyme premix: | 2 μL |
| Ultrapure water: | Add to 10 μL |
| Total: | 10 μL |

5° C. for 15 min, after the linking reaction is completed, take 5 μL of linked product to transform into competent cells *E. coli* DH5α.

V. *E. Coli* Competent Transformation
- (4.1) Take the competent cells *E. coli* Dh5α out of −80° C., add 1 μL of the plasmid to the competent cells, and place on ice for 30 min.
- (4.2) Take out the competent cells from the ice and heat shock them in a water bath kettle at 42° C. for 1 min.
- (4.3) After heat shock, put it back on ice quickly, keep for 2-5 min, add 500 μL of SOC medium, mix well, and transfer to a 50 mL centrifugal tube.
- (4.4) Incubate the 50 mL centrifugal tube on a shaker at 37° C., 150 rpm, for 45-60 min.
- (4.5) Add 25 ug/mL zeocin into the medium and pour onto a flat plate.
- (4.6) Centrifuge at 12,000 rpm for 1 min after the incubation. Discard part of the supernatant and leave around 100 μL of liquid. Suspend the broth, spread plate, and culture at 37° C.

VI. Yeast Transformation
- (5.1) Add 1 mL of overnight culture of *Pichia pastoris* GS115 to 50 mL YPD medium and incubate at 30° C., at 200 rpm for 16h.
- (5.2) At the end of 16 h culture, observe the growth of the strain, transfer 1-2 mL of seed culture to the fresh 50 mL YPD, and continue to culture for two generations until $OD_{600}$ is 1-1.5, then prepare *Pichia pastoris* competent cells.
- (5.3) Pour all the seed culture into 50 mL centrifugal tubes respectively, and place on ice for 15 min.
- (5.4) Centrifuge at 4° C., 1500×g for 5 min, and remove the supernatant.
- (5.5) Wash the strain with sterilized pre-cooled ultrapure water, and centrifuge under the same conditions as above.
- (5.6) Repeat step (5.5).
- (5.7) Add 8 mL mixed liquor (100 mM LiAc, 10 mM DTT, 0.6 mM sorbitol, and 10 mM Tris pH=7.5) to wash the strain, centrifuge at 4° C., 1500×g for 5 min, and remove the supernatant. The mixed liquor helps increase the permeability of yeast cells.
- (5.8) Wash the strain with pre-cooled 1 mol/L sorbitol, centrifuge at 4° C., 1500×g for 5 min, and remove the supernatant.
- (5.9) Repeat step (5.8).
- (5.10) Add 700 μL sorbitol-suspended cells and pre-cool on ice, to finish the preparation of the competent cells.
- (5.11) Divide the strain solution into 40/80 L portions in the pre-cooled 1.5 mL centrifugal tube each, add 5/10 μL linearized DNA, mix gently, and incubate on ice for 5 min.
- (5.12) Add the incubated solution to the pre-cooled MicroPulser cuvette (2 mm/4 mm) and prepare 1 mL of 1 mol/L sorbitol.
- (5.13) After the pulse, add the pre-cooled sorbitol immediately, pipette, suck out all the solution, and add it to a new 1.5 mL centrifugal tube.
- (5.14) Incubate at 30° C. for 1-4h.
- (5.15) At the end of the incubation, centrifuge at 12000 rpm for 1 min, discard part of the supernatant with 100 μL kept, and then spread the rest. Incubate at 30° C. for 2-3d.

VII. Induced Expression of the Strain
- (6.1) Pick a monoclonal colony containing expression cassettes grown on a selective plate as described in step VI (step VI) and transfer it to 5 mL YPD medium containing 100pg/mL antibiotics for overnight culture at 220 rpm, 30° C.
- (6.2) Transfer 1% of the overnight culture mentioned above into 50 mL BMG medium and culture for 16-20h.
- (6.3) Measure the $OD_{600}$ value of the broth in the BMG medium, and then sample cells by centrifuging at 2000×g for 10 min.
- (6.4) Then transfer it to 75 mL fresh BMM medium, adjust the initial cell concentration of the medium to $OD_{600}=4$, and shakely culture at 30° C., 220 rpm.
- (6.5) Take 500 μL of broth at 0, 48 h, 72 h, 96 h, 120 h, 144 h, and 168 h respectively (according to the experiment requirements, the time can also be extended or at other time points), centrifuge at 12,000 rpm for 1 min, retain the supernatant, and freeze it to −80° C. for subsequent liquid chromatography analysis. At the same time, take 400 μL of the solution to measure the biomass. In addition, 1% (v/v) methanol is added to the medium every 24h to provide sufficient carbon sources for the strain.

VIII. High Performance Liquid Chromatography (HPLC) Related Operations

HPLC analysis is performed using Shimadzu's LC-20AD system (Shimadzu, Tokyo, Japan) equipped with the SPD-M20A UV/Vis detector and the C18-H column (Venusil MP C18(2) 5 um 4.6×250 mm). The elution conditions are that the sample volume is 50 μl, the mobile phase is isocratic elution with ultrapure water and methanol (80:20, v/v), with the flow rate at 0.8 ml/min, and the column temperature is 25° C. The signals of cordycepin and its deamination products are detected at 260 nm.

IX. Mass Spectrometry Detection Related Operations

LC-MS detection is conducted by TSQ Quantum Ultra quadrupole Mass Spectrometer (Thermo Scientific, San Jose, CA, USA) with a Vanquish UPLC system (Thermo Scientific, Germany). Xcalibur 4.2 SP1 software (Thermo Scientific, USA) is used to collect and analyze data. Mass spectrum conditions: the capillary voltage is 3 kV, the capillary temperature is 300° C., the evaporator temperature is 250° C., the sheath gas pressure is 35, and the auxiliary gas pressure is 10.

X. Primer

The primers in the follow-up embodiments are listed in Table 1.

TABLE 1

Primers

| Primers | Primer Sequence (5'-3') |
| --- | --- |
| Cm1-F | ATTATTCGAAACGAGGAATTCATGGCCATGAACGAAAACGG |

TABLE 1-continued

Primers

| Primers | Primer Sequence (5'-3') |
|---|---|
| Cm1-R | GTACACTAATCTATTAGGCGATACCAACCTTG |
| RPS25Att-F | CGCCTAATAGATTAGTGTACATCTGATAATATAGT |
| RPS25Att-R | TCCTGCATGCACTAGTGCTAGCGTCAAAT |
| FLD1-F | TAGCACTAGTGCATGCAGGAATCTCTGGCAC |
| FLD1-R | GACAGGACATTGTGAATATCAAGAATTGTATGAAC |
| Cm2-F | GATATTCACAATGTCCTGTCCAACTTCTGC |
| Cm2-R | GGCGGCCGCCGCGGCTCGAGGTACCTTACTATCTGTGT TGAGTCCTGG |
| Cm1-con-F | TCGAAACGAGGAATTATGGCCATGAACGAAAACGG |
| Cm1-con-R | TGGGCCACGTGAATTCTATTAGGCGATACCAACCTTG |
| Cm2-con-F | TCGAAACGAGGAATTATGTCCTGTCCAACTTCTGC |
| Cm2-con-R | TGGGCCACGTGAATTTTACTATCTGTGTTGAGTCCTGG |
| GAP-FLO1-F | CAAAACACAGGCGCGATGACAATGCCTCATCGCTATAT G |
| GAP-FLO1-R | TTAAACAGTGGCGCGTTAAATAATTGCCAGCAATAAGG AC |
| DAS2-FLO1-F | ACATCAAAAGGCGCGATGACAATGCCTCATCGCTATAT G |
| DAS2-FLO1-R | TTAAACAGTGGCGCGTTAAATAATTGCCAGCAATAAGG AC |

Example 1 Construction of a Strain for Heterologous Synthesis of Cordycepin and 3'-Deoxyinosine by *Pichia pastoris*

Enzymatic encoding genes related to cordycepin synthesis are derived from the filamentous fungus *Cordyceps militaris*. The cordycepin deamination product 3'-deoxyinosine is formed by removing the amino group of the base in cordycepin with the endogenous deaminase of *Pichia pastoris*, and both products can be secreted into the extracellular supernatant of *Pichia pastoris*.

The gene fragments for cordycepin synthesis can be obtained through PCR amplification with upstream and downstream primers. To efficiently express Cm1 and Cm2 fragments derived from *Cordyceps militaris* in *Pichia pastoris* system, the present invention optimizes the codons through a whole gene synthesis method, and obtains the fragments through primer amplifications (Table 1). Since *Pichia pastoris* itself cannot synthesize cordycepin, in order to enable the *Pichia pastoris* to synthesize cordycepin, Invitrogen Company's pPICZA expression system (other expression vectors can also be constructed or used) is used, to amplify the promoter and terminator fragments, using *Pichia pastoris* GS115 genomic DNA as a template with primers in Table 1. The above amplified fragments are linked to the multiple cloning sites EcoRI/KpnI of the vector pPICZA through In-Fusion recombinase, and at the same time, Cm1 and Cm2 from *C. militaris* L5111 are respectively codon-optimized via *Pichia pastoris* bias and linked to the EcoRI site of the vector pPICZA. Plasmids pPICZA-Cm1-Cm2, pPICZA-Cm1, and pPICZA-Cm2 are obtained respectively. Positive transformants are screened by antibiotics and finally sent to BGI for sequencing to verify the correctness of the sequence. The construction process is shown in FIG. 1.

After the linearization for the correctly verified plasmids mentioned above, linearized fragments are integrated into the genome of GS115 (his4, Mut$^+$) (preserved in this laboratory) through electroporation. After antibiotic screening, a transformant THP-292 simultaneously expressing Cm1 and Cm2, a transformant PP-Cm1 expressing Cm1 alone, and a transformant PP-Cm2 expressing Cm2 alone are respectively obtained. In addition, the empty plasmid pPICZA is also transformed into the yeast to obtain a transformant PP-Con. The obtained positive transformants are preserved in 20% (v/v) glycerol.

Figure 2A:
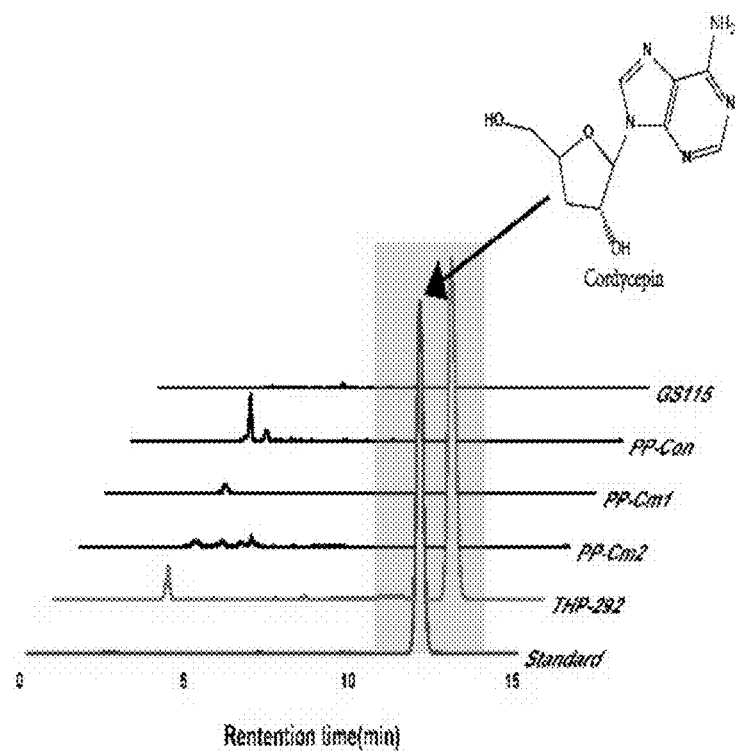
FIG. 2A is an HPLC detection spectrogram of cordycepin in fermentation broth of the engineering yeast strain THP-292.
Figure 2B:
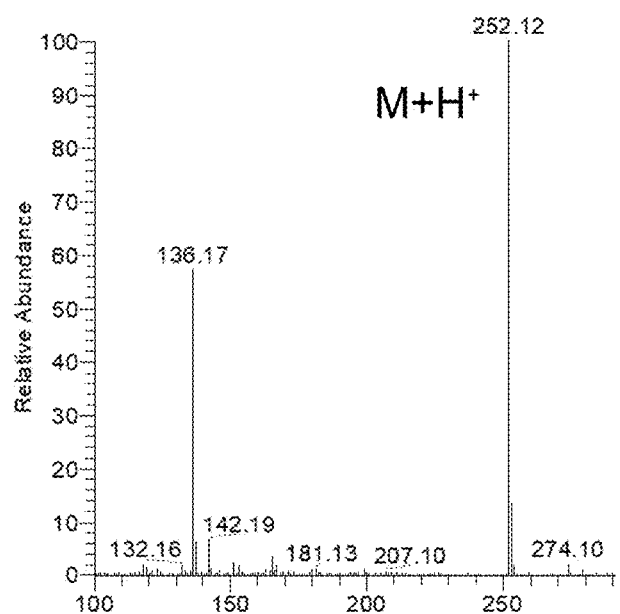
FIG. 2B is a mass spectrometry identification diagram of cordycepin in fermentation broth of the engineering yeast strain THP-292.

The obtained transformants are cultured in YPD liquid medium for 24h, and 1% (v/v) broth was inoculated into 50 mL BMG medium, cultured for 16-24h for enlarged cultivation. The above cultured products are centrifuged, and the cells are collected and transferred to 75 mL BMM induction medium for expression, and the fermentation broth was tested by HPLC. The results show that only the transformant simultaneously expressing Cm1 and Cm2 is consistent with the peak position of the cordycepin standard, while the yeast strain only expressing Cm1 or Cm2, or transferring one empty plasmid only, has no peak at the corresponding retention time. LC-MS results confirm that the molecular weight of this peak is consistent with that of a cordycepin standard sample, and this peak proved cordycepin (FIG. 2A and FIG. 2B).

Figure 3A:
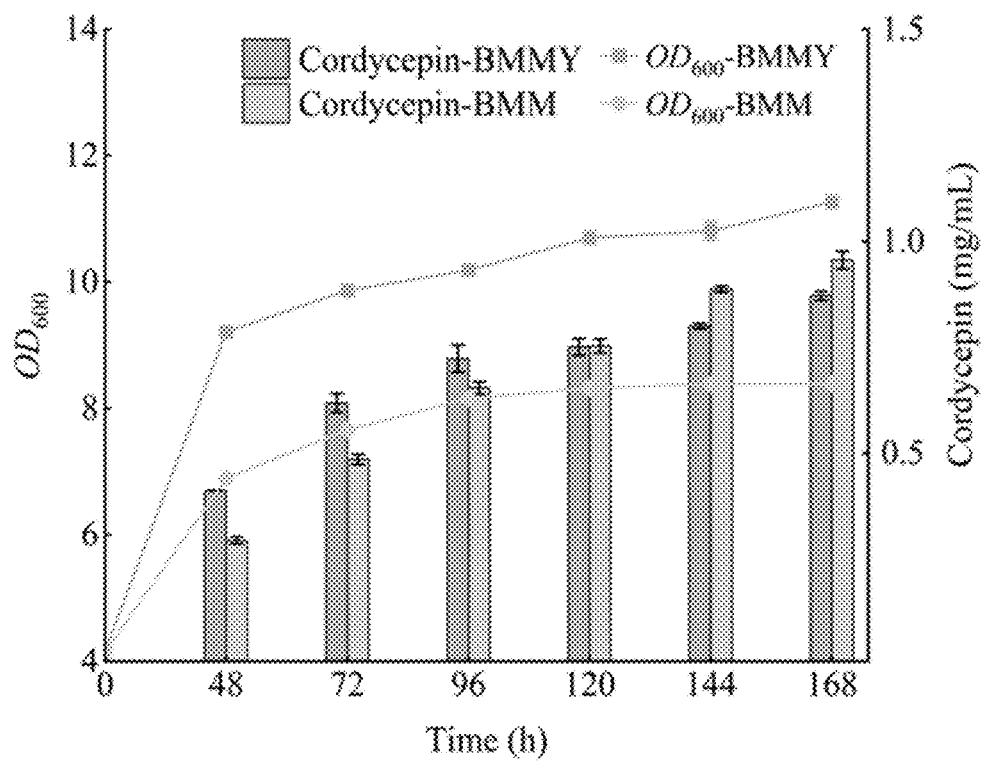
FIG. 3A is a schematic diagram of time-varying changes in producing cordycepin through fermentation of the engineering yeast strain THP-292.

The BMMY medium is usually used for expressing secreted proteins, and is rich in peptone and yeast extract. However, peptone or yeast extract is expensive and not suitable for industrial strain culture. Therefore, we culture them in the BMMY and BMM media respectively and compare the difference in cordycepin yield therebetween. THP-292 is cultured in BMMY and then in BMM for 168h, and HPLC detection shows that the contents of cordycepin produced by fermentation of the strain on these two media are 0.871±0.01 g/L and 0.956±0.02 g/L respectively (FIG. 3A), and the measured $OD_{600}$ is between 8.0 and 11.0. Hence, it is indicated that the BMM medium is more suitable for fermentation of the yeast engineering strain of the present invention.

Figure 2C:
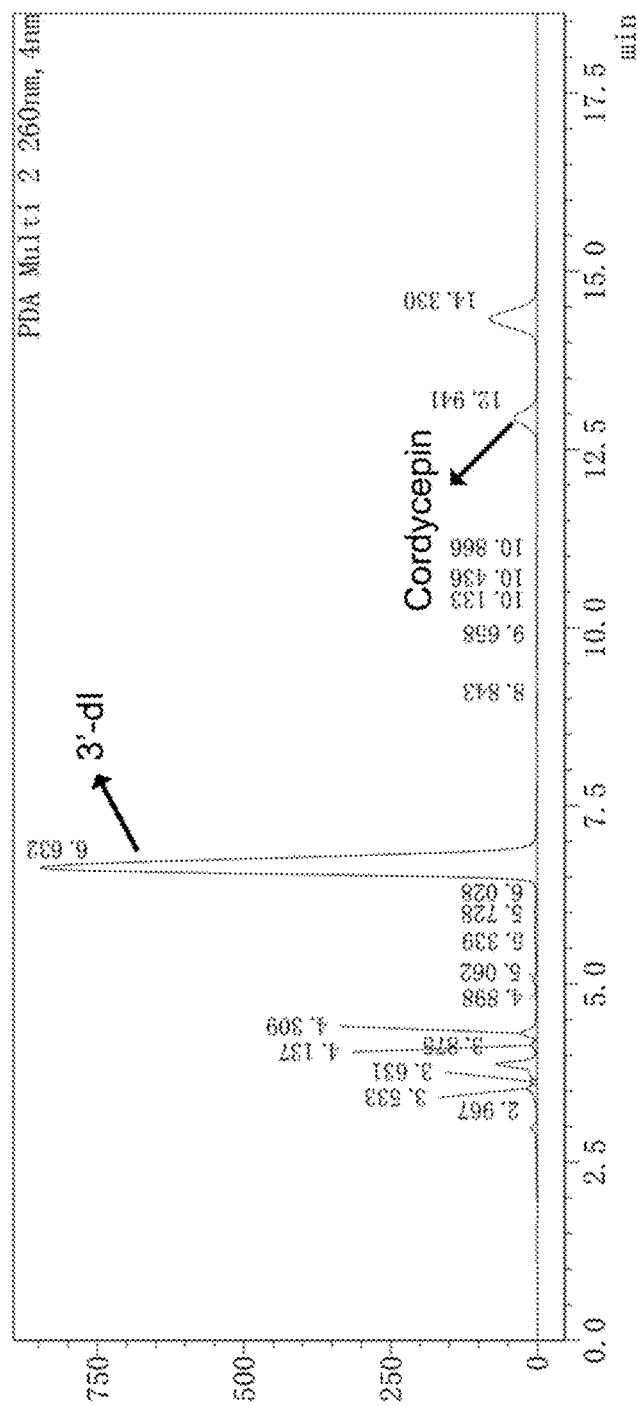
FIG. 2C is an HPLC detection spectrogram of 3'-deoxyinosine in fermentation broth of the engineering yeast strain THP-292.
Figure 2D:
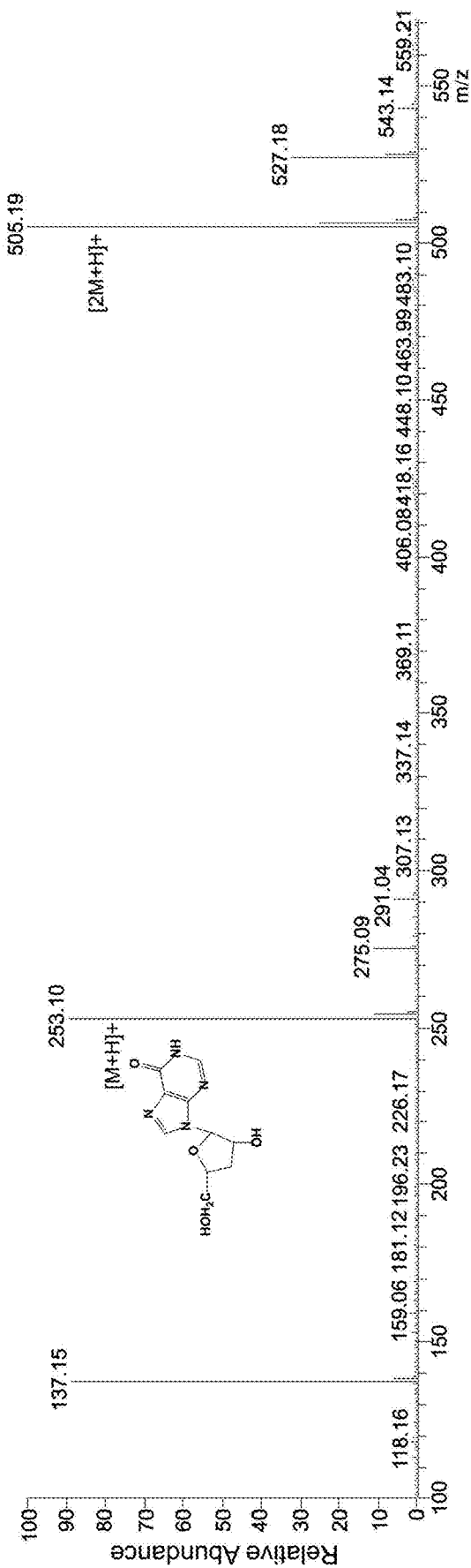
FIG. 2D is a mass spectrometry identification diagram of 3'-deoxyinosine in fermentation broth of the engineering yeast strain THP-292.
Figure 2E:
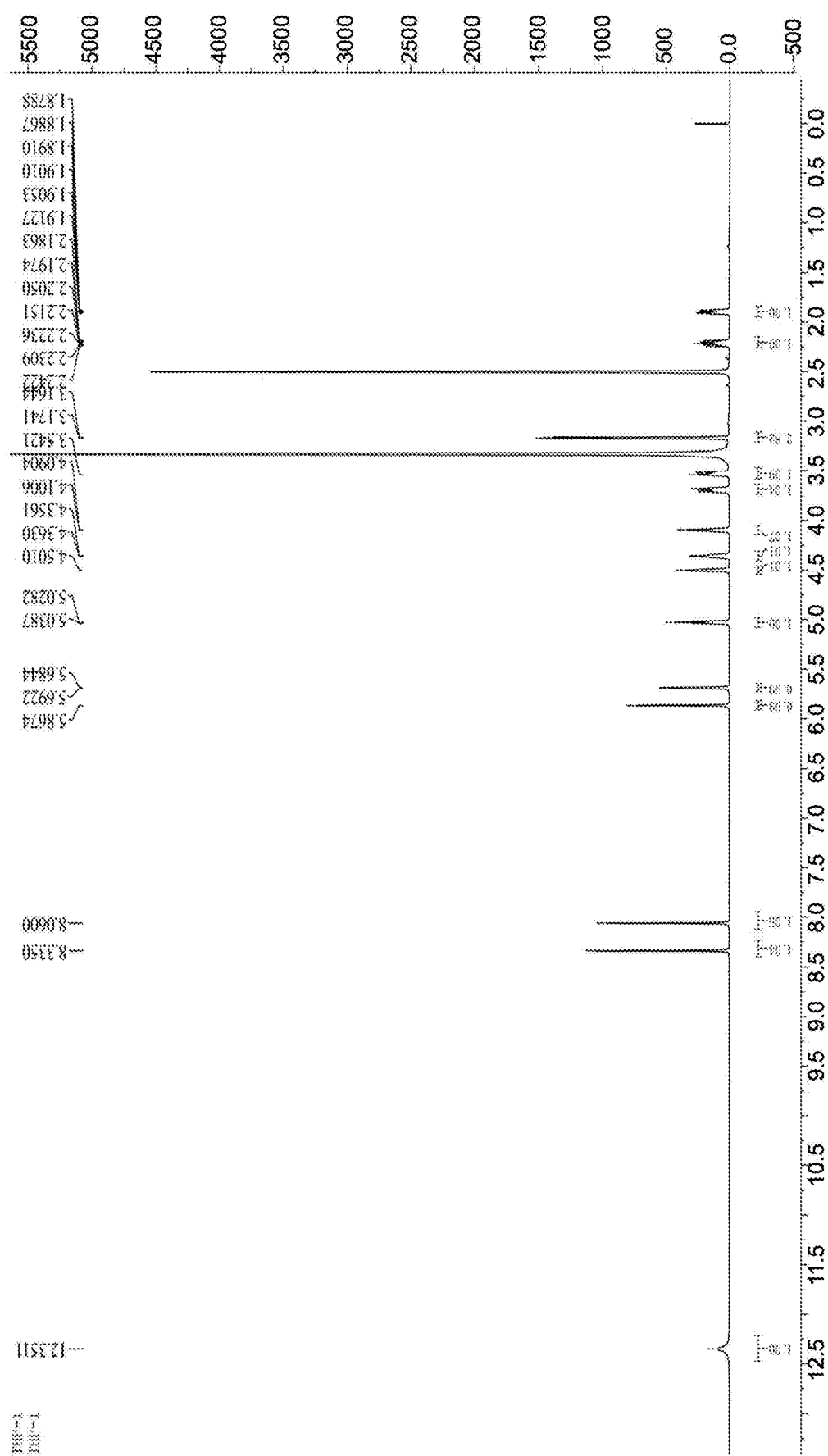
FIG. 2E is a $^1H$ NMR spectrogram of 3'-deoxyinosine in fermentation broth of the engineering yeast strain THP-292.
Figure 3B:
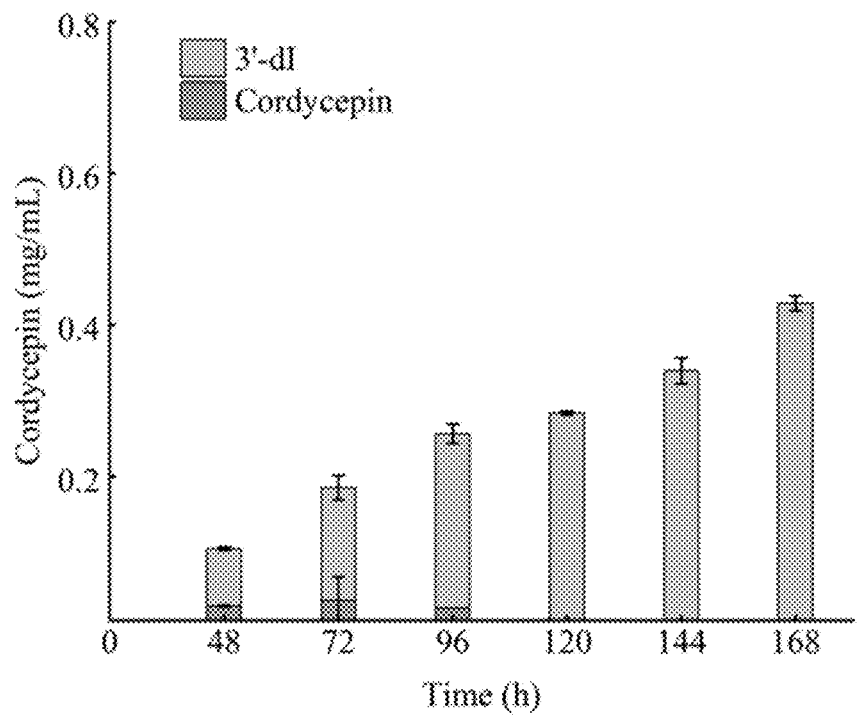
FIG. 3B is a schematic diagram of time-varying changes in producing 3'-deoxyinosine through fermentation of the engineering yeast strain THP-292.

The initial pH is adjusted to 7.0, and the THP-292 strain is switched to the 3'-deoxyinosine production mode over time. As shown in FIG. 3B, after 168h, the 3'-deoxyinosine yield is close to 0.5 g/L. The structural proof is shown in FIG. 2C to FIG. 2E. This is the first time that the existence of 3'-deoxyinosine has been reported in *Pichia pastoris* which can be secreted extracellularly and can be easily isolated, providing a reliable fermentation production source for rigid ring bio-based material monomers. Compared with cordycepin, it does not require amino protection and saves synthesis steps.

It can be seen that *Pichia pastoris* has great advantages in producing cordycepin and its derivatives:

(1) High titer and short production time: it has been reported that the yield of cordycepin in the *Saccharomyces cerevisiae* expression system after optimization is only about 0.1 g/L, and the fermentation time is 3-7d; the cordycepin yield in liquid fermentation by *Cordyceps militaris* is between 0.1-1.0 g/L, while the fermentation time is 30-40d; the fermentation time of *Pichia pastoris* can be shortened by more than ⅔ compared with *Cordyceps militaris*. The unoptimized shake flask system has reached a yield of nearly 1.0 g/L (after optimization, the yield of the shake flask is close to 2.7 g/L), with $OD_{600}$ between 8 and 12 which can reach about 100 in the fermentation tank under high density culture for Pichia pastoris, with yield at 5-10 g/L. Therefore, the Pichia pastoris system has great advantages in both production titer and productivity for cordycepin synthesis.

(2) The simple component of fermentation medium is conducive to subsequent separation: Cordyceps militaris, the filamentous fungal system, has high requirements on the medium system. The medium component is complex, with a lot of organic components and complicated metabolites, and there are a lot of extracellular polysaccharides and other substances that would interfere with subsequent separation of cordycepin. Moreover, on the one hand, Pichia pastoris can use cheap methanol as a carbon source, particularly considering the technology of converting carbon dioxide into one-carbon methanol is becoming increasingly mature, and subsequently a green process of using carbon dioxide to produce cordycepin and its derivatives may be realized. On the other hand, Pichia pastoris can use FM22 or BSM mixed salt fermentation system, with ammonium salt as the nitrogen source, and the synthesized inorganic culture system will further reduce the complexity of the separation system. Moreover, it is found through determination that more than 95% of cordycepin and its derivatives are extracellular in Pichia pastoris, which realizes further application of the fermentation-separation coupling technology.

Example 2 Construction of the Self-Flocculating Pichia pastoris Engineering Strain Flocculation of strains refers to that the cells can naturally settle and separate from the supernatant at the end of fermentation, simplifying the centrifugation step. Flocculation has great significance in three aspects: (1) it is of great significance in energy saving and emission reduction. Centrifugal separation is time-consuming and energy-intensive, and flocculation can simplify the centrifugation step; (2) the flocculating strains can achieve in-situ fermentation-separation coupling through a simple solid-liquid separation apparatus, timely relieve product-inhibition effect, and further improve production intensity; and (3) flocculation can also improve the density of cells, and a higher density of cells per unit volume can further increase the titer of the target product and shorten the fermentation time.

There are two ways to get flocculating strains: one is to add flocculant (e.g., polyacrylamide) at the end of fermentation or immobilize the cells (e.g., alginate), and the other is to screen or modify the strains to achieve self-flocculating strains, especially induced flocculation, so that flocculation will not occur earlier which can cause mass transfer resistance and affect the fermentation intensity, as compared with the constitutive flocculation strains. Self-flocculation does not introduce additional substances and has greater application potential. The flocculation mechanism of different strains is different. For example, Flo1p of Saccharomyces cerevisiae can adhere to mannan in the cell wall to initiate flocculation, while some bacteria can initiate flocculation using cellulosic substances. The FLO gene family of Saccharomyces cerevisiae are relatively well-studied flocculation genes that can encode lectin-like proteins. For example, the expression products of FLO1 protein can induce strong flocculation, while FLO5, FLO10 and the like can induce weak flocculation traits, and FLO11 can also induce filamentous growth traits, etc. The Flo1p of model yeast strain S288c (YAR050W) has 18 repeat units of 45-aa, and the greater the number of 45-aa repeat units, the stronger the flocculation. Flocculation is a reversible, asexual process that requires calcium-ion. Its N terminal can bind to mannose and beyond, and its C terminal has a GPI anchoring site.

Genes that can induce flocculation have not been reported in Pichia pastoris. There is a literature using Flo1p of Saccharomyces cerevisiae to display heterologous expression of various enzymes on the surface of Pichia pastoris. However, there is no report on complete expression of Flo1p, the realization of flocculation in Pichia pastoris, or the induction of flocculation under special conditions.

The present invention adopts an improved method which combines flocculation gene cloning and extension in the second step.

(1) Conventional cloning method: the reported longest known flocculation gene cloned by our team is used as the starting gene. This gene is derived from a self-flocculating yeast SPSC01. The 5.2kb FLO1 fragment is cloned using primers in Table 1, and the DAS2/GAP promoter and RPS3tt terminator are amplified from Pichia pastoris and Saccharomyces cerevisiae respectively. Using pPICZA-Cm1-Cm2 as the starting vector, after being digested by restriction endonuclease AscI, the promoter, the FLO1 fragment, and the terminator are sequentially linked through In-Fusion seamless cloning. Finally, the plasmid pPICZA-Cm1-FLO1-Cm2 is obtained through antibiotic screening. To integrate flocculation genes into other sites of the genome, it's only needed to replace the upstream and downstream homologous arms for the neutral sites fragments of around AOX1p and AOX1t on the vector.

Subsequently, the pPICZA-Cm1-FLO1-Cm2 plasmid is linearized and transferred into the yeast through electroporation to obtain the transformants THP-293 that simultaneously express Cm1, FLO1 and Cm2. It is found through sequencing of the flocculation gene for the transformants that the length is truncated to various degrees, and the longest fragment length is only 3.1kb. It is cultured on the YPD liquid medium for 24h, and then 1% broth is transferred to 50 mL BMG medium to culture for 16-24h for enlarged cultivation. The broth is centrifuged, and the cells are collected and transferred to 75 mL BMM induction medium for expression. The flocculation of the strain in the medium can be observed. It is found that the fermentation broth is still turbid and has slight flocculation, indicating that it is difficult to get access to expression of the flocculation gene in Pichia pastoris through conventional cloning. It has been reported that the flocculation value of Pichia pastoris engineered by similar methods is only around 5%.

Method of determining flocculation value: after centrifugation, the cells are washed twice with 0.1 mol/L sodium citrate salt (pH=5.0) and suspended, the $OD_{600}$ is adjusted to 1.5, and the accurate $OD_{600}$ value is denoted as A; the cells are centrifuged again, washed once with 0.1 mol/L $CaCl_2$ solution, and then resuspended in an equal volume. After standing for 5 min, sample at the lower end of the concave liquid surface, and measure the $OD_{600}$ value again which is designated as B, giving the flocculation value as $1-B/2A$.

(2) Improved method which combines flocculation gene cloning and extension in the second step: the FLO1 sequence is analyzed, with a total of 22 135 bp repeat regions (corresponding to the 45-aa product), and codon adjustment is made to make the gene sequences of each repeat regions as different as possible. The GGAG-GAGGTGGTTCC sequence (translated as GGGGS) is inserted in the middle between the 11st and 12th repeat region during fully synthesizing the FLO1 gene, and the expression vector is constructed as above. Note that the slow-growing DH5α strain is chosen as the E. coli host cell to retain the original length of FLO1 to the greatest extent. As above, transformed into the host yeast to obtain GS115-FLO.

After that, the gRNA is designed that the last three bases TCC of the bases encoding GGGGS as the PAM region. Any CRISPR/Cas9 vector can be used to construct homologous arms targeting both ends of GGGGS (400 bp each). The linearized donor DNA is obtained by directly gene synthesis, including upstream and downstream homologous arms and 12 repeat units of 135 bp in the FLO gen. The gRNA plasmid and the Cas9 plasmid are co-transformed into GS115-FLO, and the transformant GS115-FLOE is obtained as above. Colony PCR is performed to amplify the flocculation genes, and 2.6-4.6kb flocculation genes can be obtained to fulfill various degrees of flocculation. The measured flocculation value is between 5% and 75%. The positive transformants with the longest flocculation gene show obvious flocculating traits, and the size of flocculating particles may reach beyond millimeter-level and would not collapse after shaking.

Example 3 Optimization of Induced Fermentation Medium

The medium is essential to microbial growth and reproduction, and biosynthesis of various metabolites. The composition of the medium has an important impact on the growth of strains and the production of metabolites. Therefore, this inventor optimizes the composition of induction medium and culture conditions respectively.

Taking cordycepin as an example, in following experiments, optimization is conducted by the single-factor control variable method. Cultivation is under 30° C. and 180 rpm for 168h, and the biomass is measured with a spectrophotometer. The optimization of 3'-deoxyinosine production can be conducted with reference to the above.

Figure 4A:
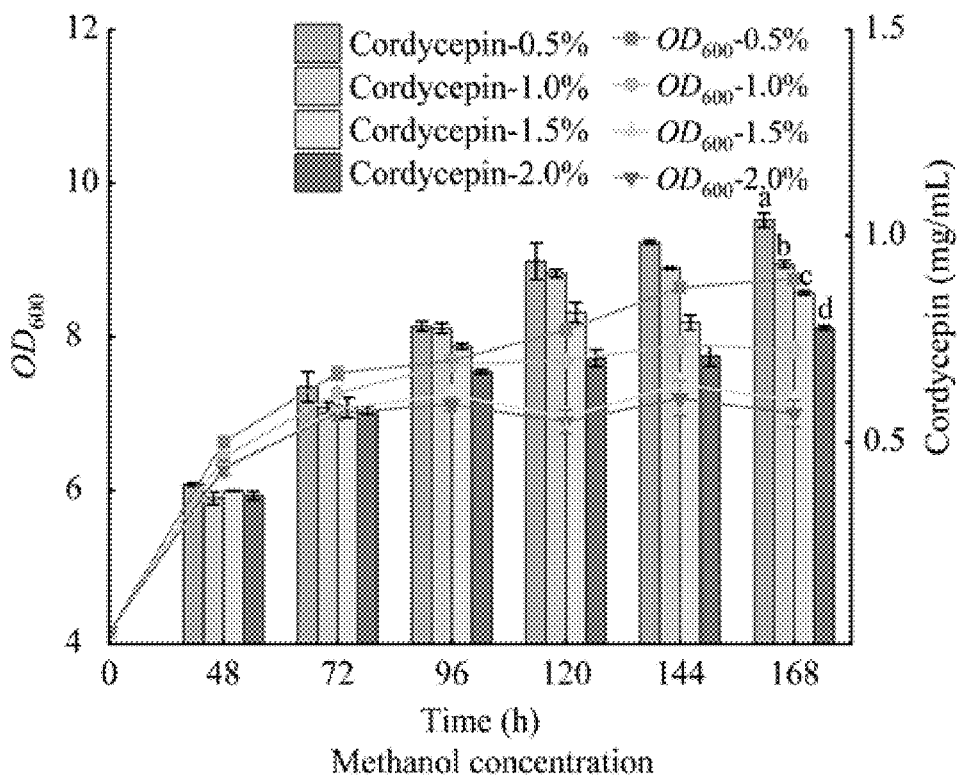
FIG. 4A is a schematic diagram of time-varying changes of cordycepin producing in fermentation medium under methanol addition concentration optimization.

3.1 Keep other components unchanged, the addition amount of methanol in the induction medium is set to be 0.5%, 1.0%, 1.5%, and 2.0%. Each performs in triplicate. As shown in FIG. 4A, the cordycepin expression amount reaches the highest level with the methanol concentration at 0.5%.

Figure 4B:
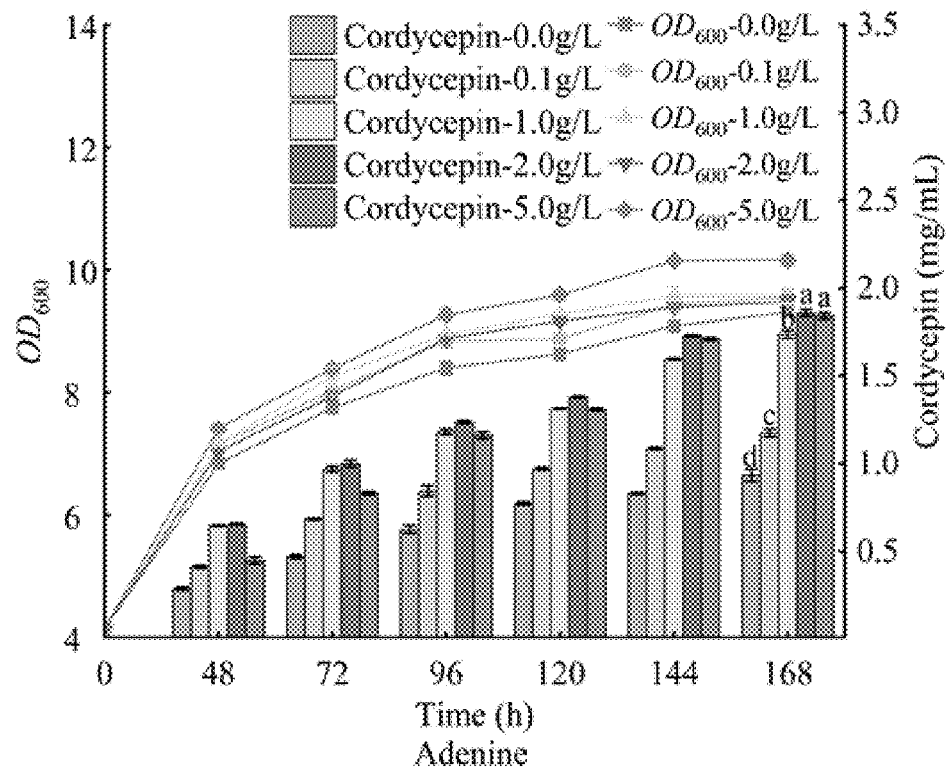
FIG. 4B is a schematic diagram of time-varying changes of cordycepin producing in fermentation medium under adenine addition concentration optimization.

3.2 Keep other components unchanged, the addition amount of adenine in the induction medium is set to be 0 g/L, 0.1 g/L, 1.0 g/L, 2.0 g/L, and 5.0 g/L. Each performs in triplicate. As shown in FIG. 4B, the expression level of cordycepin is significantly higher than that of the control at 1.0 g/L-5.0 g/L, and the content of cordycepin reaches the highest when the addition amount of adenine is 2.0 g/L.

Figure 4C:
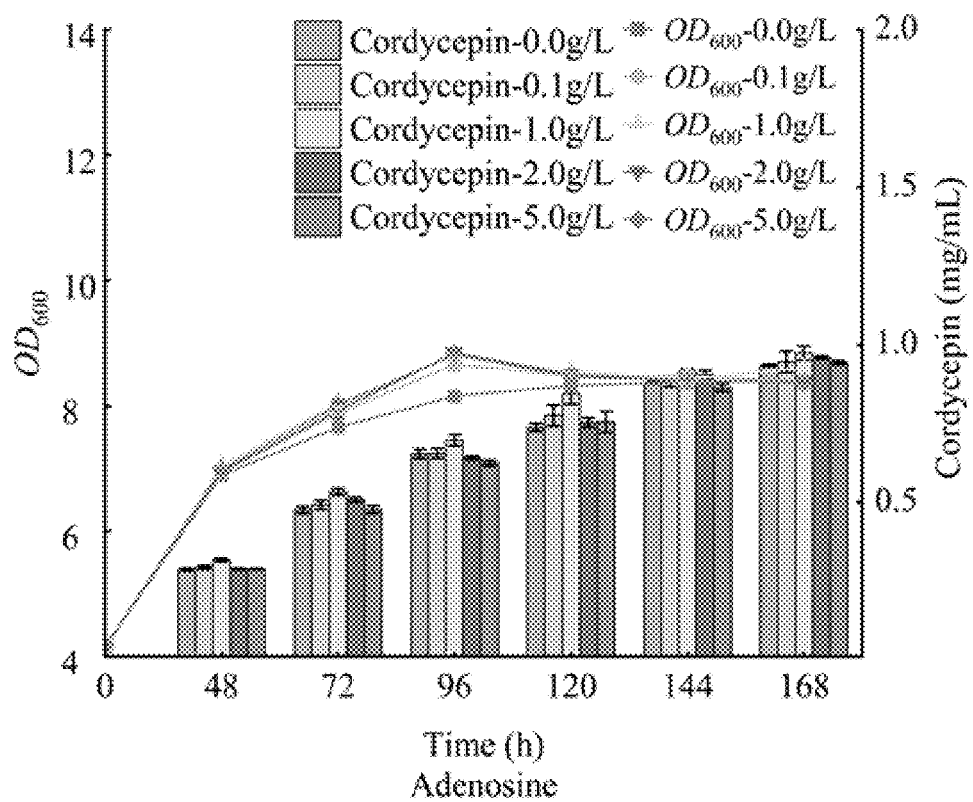
FIG. 4C is a schematic diagram of time-varying changes of cordycepin producing in fermentation medium under adenosine addition concentration optimization.

3.3 Keep other components unchanged, the addition amount of adenosine in the induction medium is set to be 0 g/L, 0.1 g/L, 1.0 g/L, 2.0 g/L, and 5.0 g/L. Each performs in triplicate. As shown in FIG. 4C, when the addition amount of adenine is 1.0 g/L, the cordycepin content reaches the highest.

Figure 4D:
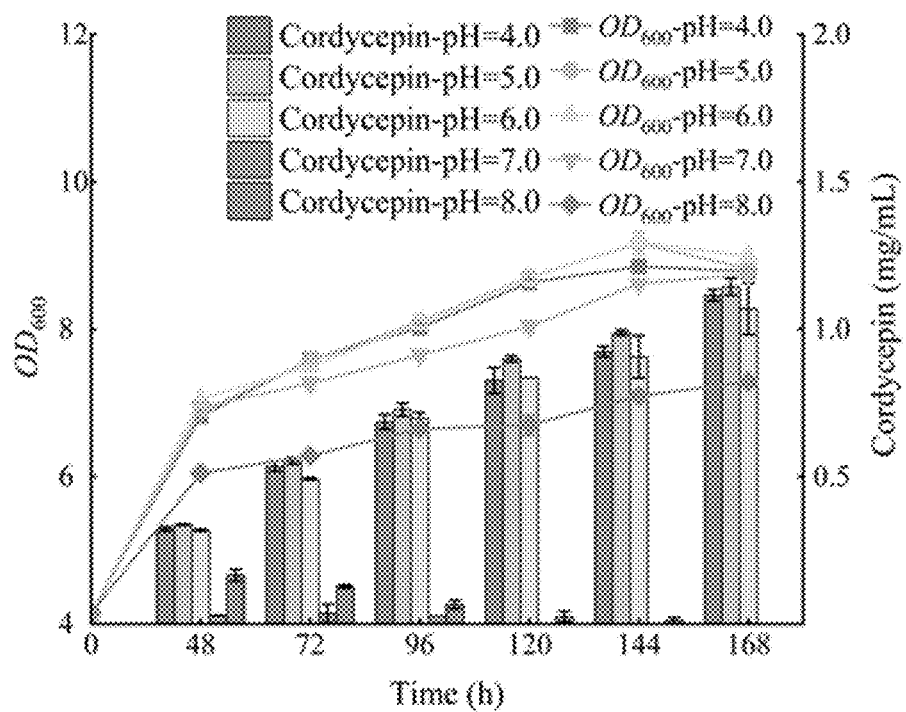
FIG. 4D is a schematic diagram of time-varying changes of cordycepin producing in fermentation medium under initial pH optimization.

3.4 Keep other culture conditions unchanged, the initial pH value of the induction medium is set to be 4.0, 5.0, 6.0, 7.0, and 8.0. Each combination performs in triplicate. As shown in FIG. 4D, when the initial pH value of the induction medium is 4.0-6.0, the amount of cordycepin is significantly higher than that of the other two groups, and when pH=5.0, the content of cordycepin reaches the highest. When the pH is greater than or equal to 7.0, the production mode is converted to 3'-deoxyinosine synthesis.

Figure 4E:
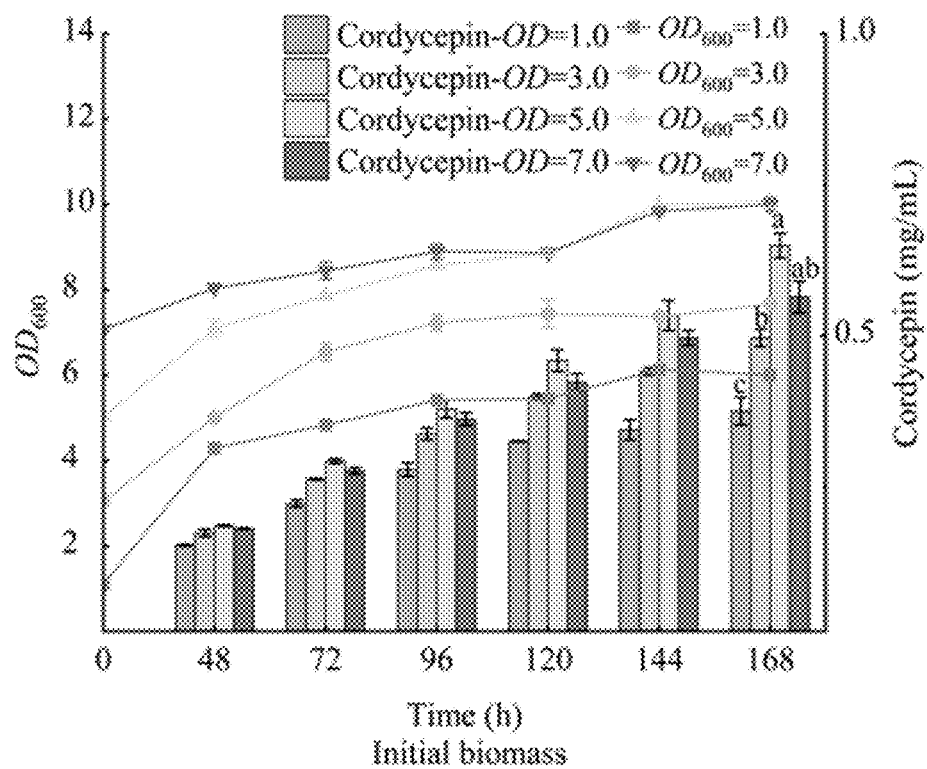
FIG. 4E is a schematic diagram of time-varying changes of cordycepin producing in fermentation medium under inoculum volume addition concentration optimization.

3.5 Keep other culture conditions unchanged, the initial cell concentration $OD_{600}$ of the induction medium is set to be 1.0, 3.0, 5.0, and 7.0. Each performs in triplicate. As shown in FIG. 4E, when the initial cell concentration $OD_{600}$ in the induction medium is 5.0, the content of cordycepin reaches the highest.

Figure 4F:
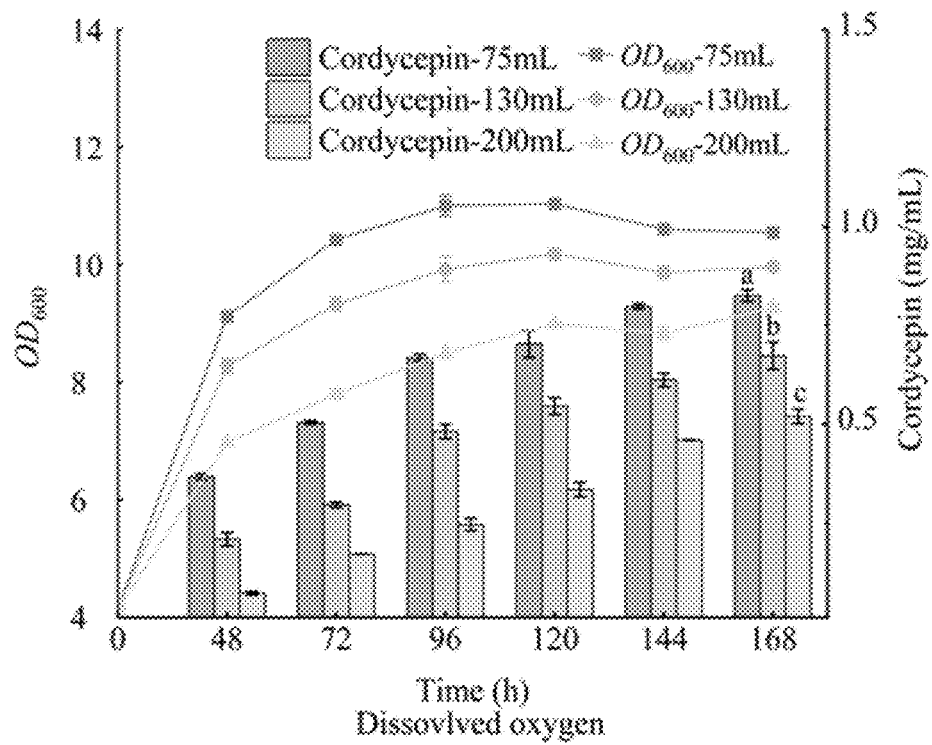
FIG. 4F is a schematic diagram of time-varying changes of cordycepin producing in fermentation medium under shake flask liquid filling amount optimization.

3.6 Keep other culture conditions unchanged, the liquid filling amount of medium is set to be 75 mL, 130 mL, and 200 mL. Each performs in triplicate. As shown in FIG. 4F, when the liquid filling amount is 75 mL, the content of cordycepin reaches the highest.

Figure 4G:
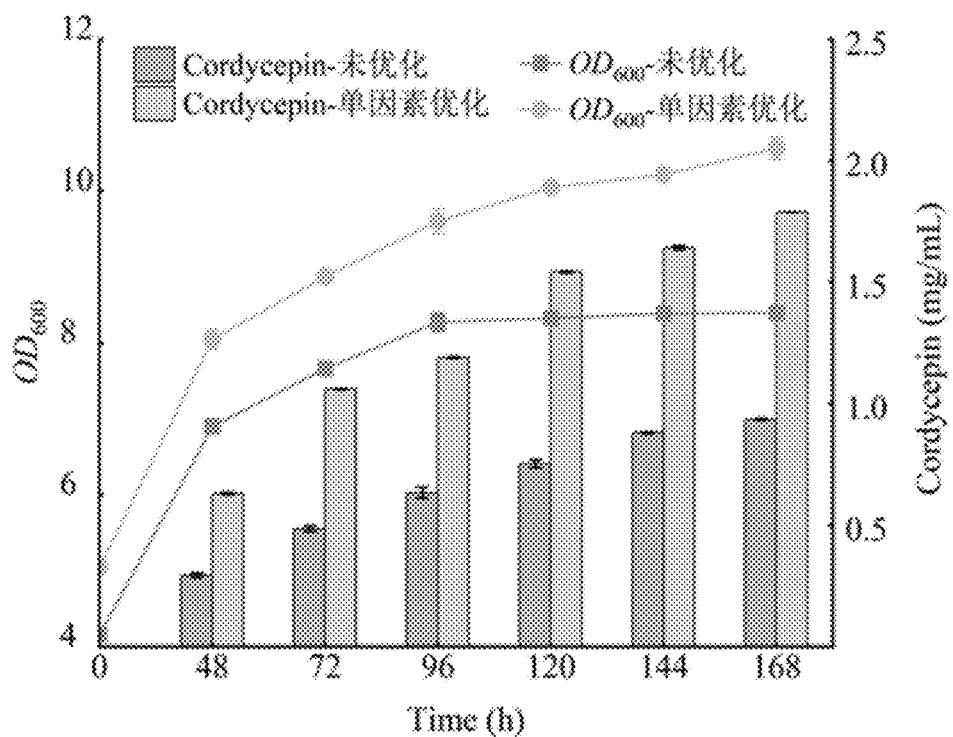
FIG. 4G is a schematic diagram of time-varying changes of cordycepin producing in fermentation medium under in single factor optimization.

Based on the optimal conditions obtained above, after fermentation, the content of cordycepin reaches 1.78 g/L as shown in FIG. 4G, which is 86.38% higher than that of the unoptimized system.

Figure 4H:
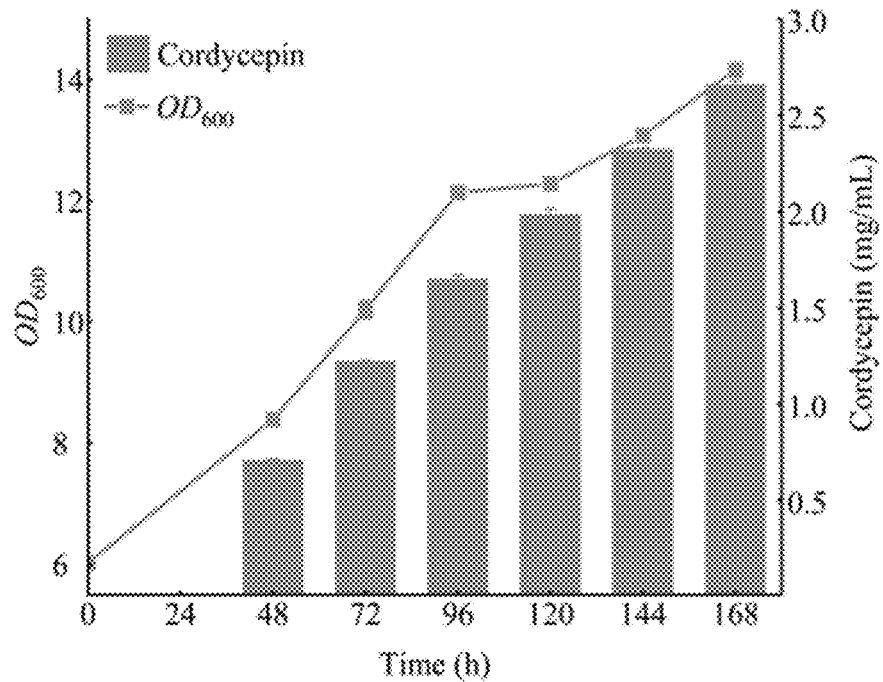
FIG. 4H is a schematic diagram of time-varying changes of cordycepin producing in fermentation medium under orthogonal experimental optimization.

Example 4 Optimal Culture Conditions for Cordycepin-Producing Unconventional Yeast Optimized by Orthogonal Experiments Based on the optimal conditions tested in the single-factor experiments of Example 3, an orthogonal table of four factors and three levels is designed to carry out fermentation experiments 9 times, and 3 parallel experiments are set for each group. The fermentation experiment is conducted according to the parameters given in Table 2. After fermentation for 168h, the supernatant of the fermentation broth is subjected to HPLC quantitative detection. The fermentation results of each group are shown in Table 3. Finally, the optimal culture conditions obtained by the experiment were verified, and the fermentation culture is carried out under this set of the culture conditions. The fermentation broth after being fermented for 168h is subjected to HPLC detection, and the results are shown in FIG. 4H. At this time, the cordycepin yield reaches 2.68 g/L, which is increased by 180.63% compared with the unoptimized system.

TABLE 2

Orthogonal experiment design of fermentation conditions for recombinant strains producing cordycepin

| | Factor | | | |
| --- | --- | --- | --- | --- |
| Level | A (methanol concentration %) | B (initial pH) | C (adenine g/L) | D (initial $OD_{600}$) |
| 1 | 0.25 | 4.0 | 2 | 4.0 |
| 2 | 0.5 | 4.5 | 3 | 5.0 |
| 3 | 0.75 | 5.0 | 4 | 6.0 |

TABLE 3

Orthogonal test results

| | Factors | | | | |
| --- | --- | --- | --- | --- | --- |
| Test Number | A | B | C | D | Cordycepin (mg · $L^{-1}$) |
| 1 | 1 | 1 | 1 | 1 | 1709 |
| 2 | 1 | 2 | 2 | 2 | 1856 |
| 3 | 1 | 3 | 3 | 3 | 1847 |
| 4 | 2 | 1 | 2 | 3 | 2642 |
| 5 | 2 | 2 | 3 | 1 | 2254 |
| 6 | 2 | 3 | 1 | 2 | 2513 |
| 7 | 3 | 1 | 3 | 2 | 2381 |
| 8 | 3 | 2 | 1 | 3 | 2529 |
| 9 | 3 | 3 | 2 | 1 | 2355 |
| K1 | 1.804 | 2.244 | 2.250 | 2.106 | |
| K2 | 2.470 | 2.213 | 2.284 | 2.250 | |
| K3 | 2.422 | 2.238 | 2.161 | 2.339 | |
| R | 0.666 | 0.031 | 0.123 | 0.233 | |

Comparison of the Cordycepin Production of Different Hosts, as Shown in Table 4:

TABLE 4

Comparison of cordycepin production in different systems

| Fermentation System | Strain | Strategy | Cordycepin Titer (mg · L$^{-1}$) | Production Cycle (d) | Production Intensity (mg/(L · h)) | Separation Difficulty |
|---|---|---|---|---|---|---|
| Static liquid fermentation | C. militaris NBRC 10352-3 | Add 6.76 g · L$^{-1}$ adenosine as a precursor substance | 6 200 | 24 | 10.76 | ***** |
| | C. militaris CICC 14014 | Add 20 g · L$^{-1}$ peanut oil during fermentation | 5290 | 20 | 11.02 | ***** |
| | C. militaris CGMCC2459 | Response surface optimization of medium components and culture conditions | 2008.48 | 35 | 2.39 | ***** |
| Liquid submerged fermentation | C. militaris CCRC 32219 | | 2214.5 | 24 | 3.84 | **** |
| | C. militaris | C/N ratio optimization | 345.40 | 21 | 0.68 | **** |
| | S. cerevisiae SHC16 | Heterologous expression of ScCNS1 and ScCNS2 in Saccharomyces cerevisiae | 137.27 | 6 | 0.95 | ** |
| Shake flask liquid fermentation | P. pastoris THP-292 | Heterologous expression of Cm1 and Cm2 genes derived from Cordyceps militaris in Pichia pastoris, and optimization of the cordycepin medium components and fermentation conditions (the present invention) | 2680 | 7 | 15.95 | * |

Note:
the more * there is, the more difficult it will be for separation.

Example 5 Cordycepin Tolerance Test

Figure 5:
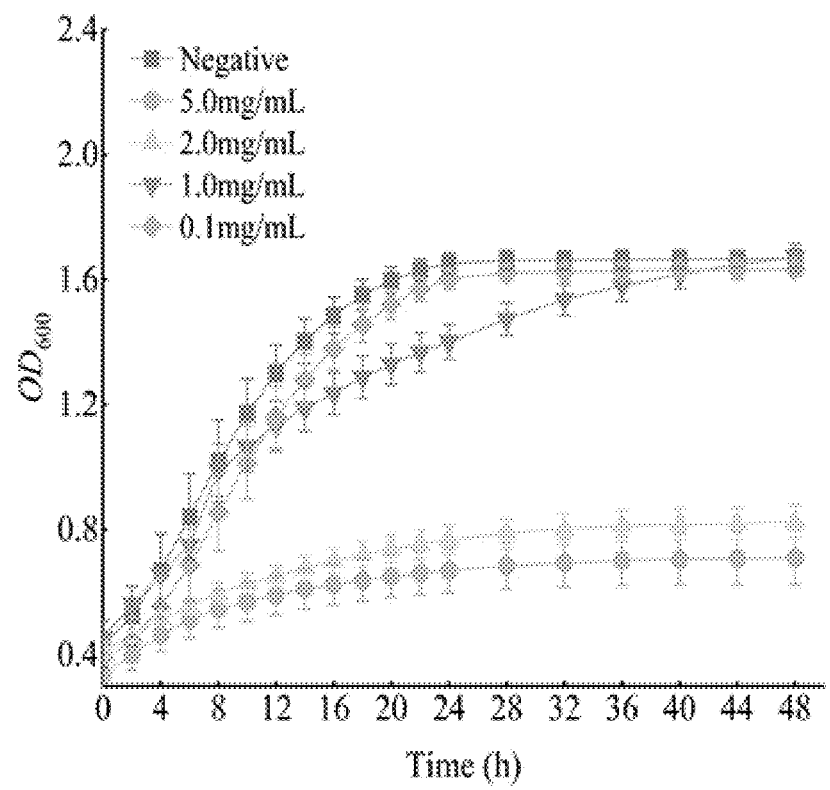
FIG. 5 is a curve showing the results of the tolerance test of *Pichia pastoris* to cordycepin.

In order to detect the tolerance of yeast strains to cordycepin, the inventor thus provides a method of detecting the tolerance of yeast strains to cordycepin. The *Pichia pastoris* GS115 strain is activated and inoculated into a 96-deep porous plate containing YPD medium, with the inoculation concentration at about OD$_{600}$=0.4, supplemented with the cordycepin solutions under different concentrations (0.1, 1.0, 2.0, 5.0 g·L$^{-1}$). The broth without cordycepin is used as the control, and the porous plate is placed into BioScreene, cultured by shaking at constant temperature of 30° C., and the biomass of the strain is measured every 2h. Triplicates are set in each group, and an average value of the triplicate is calculated to draw a growth curve of yeast strains under the effect of different concentrations of cordycepin. The results are as shown in FIG. 5, the growth of yeast strains is severely inhibited in the YPD medium containing 2-5 g/L cordycepin, and 1 g/L cordycepin has slight impact on the growth of yeast strains, while cordycepin below 0.1 g/L almost has no effect on the growth of yeast strains. As mentioned above, the cordycepin yield has exceeded 2.0 g/L, so the stress tolerance of the strain needs to be considered.

Example 6 Cordycepin Fermentation and Separation Coupling

To solve the problem of product inhibition during the cordycepin fermentation process and improve the utilization rate of raw materials in medium, the present invention provides an apparatus coupling fermentation and separation for cordycepin producing, which is mainly used for fermentation tank culture.

Figure 6:
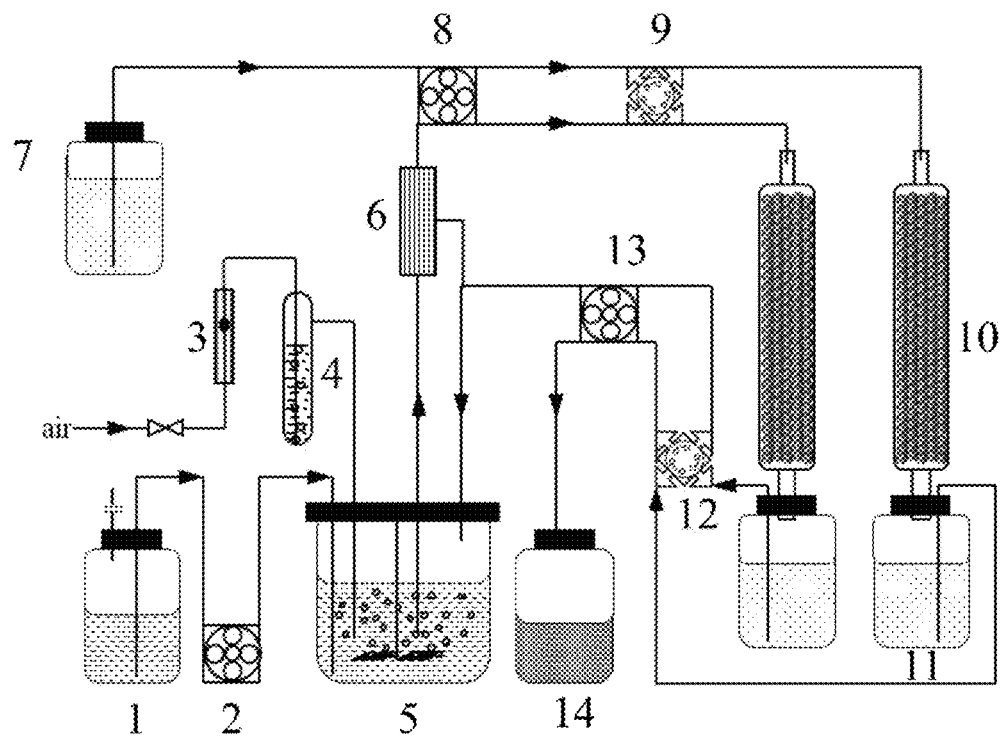
FIG. 6 is a diagram of a cordycepin fermentation, separation, and coupling apparatus.

The apparatus includes the following parts: refill bottle 1; peristaltic pump A2; rotor flowmeter 3; humidifier 4; fermentation tank 5; solid-liquid separator 6; eluent 7; peristaltic pump B8; multi-directional valve 9; adsorption separation column 10; collection bottle A11; multi-directional valve B12; peristaltic pump C13; collection bottle B14. The flow paths among the parts are connected through silicone tubes (as shown in FIG. 6).

During the operation of the apparatus, the refill bottle 1 transfers the fermentation broth components containing cordycepin to the feed port of the fermentation tank 5 through the peristaltic pump A2, and air in the air pump flows to the fermentation tank 5 through the humidifier 4. When the concentration of cordycepin reaches 1.0 g/L, the multi-directional valve 9 is turned on and the peristaltic pump B8 starts to operate at the same time, and the fermentation broth is separated from the cells through the solid-liquid separator 6, and the fermentation broth enters the adsorption separation column 10; after the adsorption is completed, the fermentation broth flows out from the discharge port of the adsorption separation column 10 into the collection bottle A11, and then the multi-directional valve B12 is turned on and the remaining fermentation broth is transferred back to the fermentation tank 5 through the peristaltic pump C13. After the adsorption is completed, the switching of the peristaltic pump B8 and the multi-directional valve A9 are adjusted to allow the eluent 7 to flow to the adsorption separation column 10 for dissociative adsorption, and finally the analytical liquid flows out from the discharge port of the adsorption separation column 10 to the collection bottle A11.

Macroporous adsorption resin NKA-II is selected as the separation medium, and the resin is used after being treated sequentially with acid, alkali and 95% ethanol. When the concentration of cordycepin exceeds 1 g/L, the above equipment is activated, the fermentation tank 5 stops stirring, and the pump system is turned on after standing for 2 min. The supernatant is kept to further separate the cells through the solid-liquid separator 6, and then the macroporous resin adsorption is started, and the flow rate is adjusted to 1-10BV/h, and the stirring resumes. The cordycepin samples with a purity exceeding 85% are obtained through elution with 95% ethanol at 1-2BV/h followed by spin evaporation and crystallization, and the total cordycepin titer reaches 5-10 g/L.

The above-mentioned embodiments are only preferred embodiments of the present invention and are not all possible embodiments of the present invention. For a person skilled in the art, any obvious modification without deviating from the principle and spirit of the present invention shall be considered within the scopes of the claims of the present invention.

The invention claimed is:

1. A preparation method for an engineering strain producing cordycepin and its derivative 3'-deoxyinosine, comprising following steps:
   (S1), optimizing both an oxidordeuctase gene Cm1 (SEQ ID NO. 1) and a metal ion-dependent phosphohydrolase gene Cm2 (SEQ ID NO. 2) of *Cordyceps militaris* L5111 according to *Pichia pastoris* codon bias, wherein a biological specimen of the *Cordyceps militaris* L5111 may be obtained from a deposit at the China Center of Type Culture Collection (CCTCC) bearing a preservation number *Cordyceps militaris* L5111 CCTCC M 2022505;
   (S2), performing PCR amplification on the genes Cm1 and Cm2 to generate a plurality of gene fragments and recovering the plurality of gene fragments through agarose gel electrophoresis;
   (S3), cloning methanol induced promoter fragments DAS2p, AOX1p, FLD1p and terminator fragments AOX1t, RPS25At, CYCt of *Pichia pastoris*; and (S4), constructing an expression vector of *Pichia pastoris*, then inserting the cloned promoter fragments DAS2p, AOX1p, FLD1p and the genes Cm1 and Cm2, into *Pichia pastoris* through a chemical or an electrical transfer, and screening to obtain an engineering strain of *Pichia pastoris* through a resistance marker carried by the expression vector, wherein a FLO1 gene from *Saccharomyces cerevisiae* is introduced into the *Pichia pastoris* whose length on the chromosome is further extended by gene editing.

* * * * *

SEQUENCE LISTING

```
Sequence total quantity: 18
SEQ ID NO: 1              moltype = DNA  length = 2379
FEATURE                   Location/Qualifiers
source                    1..2379
                          mol_type = other DNA
                          organism = Cordyceps militaris
SEQUENCE: 1
atggccatga acgagaacgc ttatccgact acatgtccat cctttgaacg ggaaaaccac   60
cgtgatgcat tgcgtcaacc ctttgacccg gcgtttcgac gcacctggtc gaatggggtg  120
gccctccgac agctcgtcga cttcccacta ccgaccgtgg ccaaccacac catgtcgtat  180
gccctgattg agtactgtct tagccgcctg ccgatgcagc acctggagcg gctgggacag  240
ctcaagattc ccgtcgagct tcacgcagcc cccttcagt acctgcagaa gcaccacggc  300
gcctttggct ttgactgggt ggagcgcttc gtctggcgaa cccacgatct gcacaagccc  360
tacaattttc tccgcccgga actgctcctg gcgcaggaat ccggctcaca gaggatcgtc  420
gccctcctca ccatcatgcc tggggaagac tacatccgcc actatgcgag catcctcgag  480
gtcgcgcagc acgacggcgc aatctcctcg catcacgagc cgatccgctg cgtgctgtat  540
ccgcacctca cgcagtccat gatggcctgg acaggactga cagagttctc cctcagcgtt  600
gagcctggcg atattctgat tctcggcttc gtcgccgagc tgctccctcg gtttgcttct  660
ctcgtgccca ccgcgcgagt cattgggcga caagacgcgc agtattacgg tcttgtccgg  720
cttgagctcc gcccggggct cgtcttcagc ctcatcggtg ccaagttcag ctactggggc  780
aacctaggcg ggcgcgtcgt ccgggagctg gccgcccgca gaccgcgcgc catctgctat  840
attgctaagc agggcaccct cctgtcgccg ggcgacatcc accgcacaat ctactcgccc  900
acccggtact gcgtctttga caagggccaa gcctgctggc acggagacga tcactcagcc  960
ctgccatca acccactctc atcgagattc cccacctttg atcgcggcct gcatgtgtcg 1020
acgcccacca tcgtggagca ggatgtcgac tttcggacac aagtggaggc ccatgcgct  1080
tcctccgttg ataacgaatt ggcgcagatg gcaagagctc tcacggacgt gcatgaagag 1140
aaccctcga tggagcgcgt ccagttgctg cctctcatgt tcattaccga ctatctccga 1200
cgcccggaag agctcggaat gacagtgccg ttcgacctta catcgcgcaa cgaaaccgtg 1260
catcgtaaca aggacttgtt cctggctagg tctgcccacc tggttctgga agcatttggt 1320
gtcatcgagc gccccaaggc catcatagtg gggacgggat atggtgtcaa gaccattctg 1380
ccagccctgc agaggcgcgg agttgaagtg gttggattgt gcggcggtcg tgaccgtgcc 1440
aagacggagg ccgtggggaa caaacacggt ataccatgca ttgatgtctc tttggccgaa 1500
gtgcaagcaa ctcacggcgc caatctgctc tttgtcgctt ctccgcacga taagcatgct 1560
gctcttgtcc aggaggccct tgacctcggc ggctttgaca ttgtatgcga gaagccactt 1620
gccttggaca tggcaacgat gcgacatttt gccaatcaat cacaaggctc ctctcagctg 1680
cgcttgatga accaccctct ccgcttctac ccgccgctca ttcagctcaa ggcggcctcc 1740
aaagaaccaa gcaacattct ggccattgaa attcagtact tgactcggcg gctgtccaag 1800
ctcacccatt ggagcgctgg cttctccaaa gccgccggag gaggcatgat gctagccatg 1860
gccactcatt tcctcgatct catcgaatgg ctcacgagtt cgtcactcac cccggcctcg 1920
gtgcaagaca tgtccacatc gaactcgatt ggtccgctac cgaccgaaga tgctggagcc 1980
accaagactc ccgatgccga gtcggccttc cagatgaacg gctgctgcgg cctgtccaca 2040
aagtactcgg tggactgtga cggtgctgca gacactgaac tattttccgt cacgctccgt 2100
cttgacaatg agcacgagct tcgatttatc cagagaaagg gaagccctgt tctgctgaa  2160
cagcgcctcc ctggccgaga atggttgccg ctcaaggttc attgggagca gcgcgtgcga 2220
gagggctcgc cgtggcaaat ctccttccag tactttgcgg aagaacttat cgaggcaatc 2280
tgcatgggaa caaggtcggc gtttgcggaa aaagccacag ggttcagcga ctatgctaga 2340
caagtcggcg tctttggatc caaggtgggc atagcctga                        2379

SEQ ID NO: 2              moltype = DNA  length = 1038
FEATURE                   Location/Qualifiers
source                    1..1038
                          mol_type = other DNA
                          organism = Cordyceps militaris
SEQUENCE: 2
atgtcttgtc ctaccagcgc cggtgtcctc cagactcacc agctcctcaa tgacaacagc   60
```

```
atcttgattc gggatgaaat ctacggggag gagctggtct cggagccagt tctcgtagag    120
ctgctccaga gcgcagaggt tcagcgactt cagggcatct gccaacacgg agtcacggga    180
ttcttgggca tcacgccgcg tgtcacacgc ctcgagcatt cggtcggtgc atttatactc    240
gtgcgaagag tcggtgccgc gctcgacgag caagtcgcag ccctactcca tgacatttct    300
cacaccactc tcagtcatgt cattgaccac gccctctcca agcctgggga gggaagctac    360
cacgaggtgc acaaggcgcg gtatctcaag acgacgcggc tgcccgacat tgtcgccaaa    420
cacggcatca gccagaaagt tttcgaagaa gagctgtttc cgctggtgga gatgccgtcg    480
cctcaactgt gcgccgaccg cctcgactac gctctacgcg acgccgtcag ctttggcaag    540
ctggccatgg aagacgccca aaaggttgtc tcgtctctcc gggcatttcc gagtgcgaca    600
acgcccggc gtctgctcgt cctcgacgcc gccgaggtcg ctctgacgct gtcccgcgca    660
tatacgacga cggacaagga tgtcggtcg aacccggccc acatcgacat gtacgagcgg    720
acgggccgc taattggcga gctggtcgag gccggctctg tcgaggacaa ggtgctgtgg    780
caggtctcgg acgccgagtt ttggacaatg ctccgcaag cagcgaaccc ggagcagcga    840
cgcgccattg agcggctgga aacggagggc gtcccagagg acgacggcct cgagctgcca    900
cactgcgcca agatccgcac tcttgaccca gacgtctggc agcgagggga aaagcaaccg    960
gcgccgctgt ccattgtgtt gccgacgtgg ggaacggagc gacagcagta cattctgagc    1020
cgcacgcagc atcgatga                                                  1038

SEQ ID NO: 3               moltype = DNA  length = 41
FEATURE                    Location/Qualifiers
source                     1..41
                           mol_type = other DNA
                           organism = synthetic construct
SEQUENCE: 3
attattcgaa acgaggaatt catggccatg aacgaaaacg g                         41

SEQ ID NO: 4               moltype = DNA  length = 32
FEATURE                    Location/Qualifiers
source                     1..32
                           mol_type = other DNA
                           organism = synthetic construct
SEQUENCE: 4
gtacactaat ctattaggcg ataccaacct tg                                   32

SEQ ID NO: 5               moltype = DNA  length = 35
FEATURE                    Location/Qualifiers
source                     1..35
                           mol_type = other DNA
                           organism = synthetic construct
SEQUENCE: 5
cgcctaatag attagtgtac atctgataat atagt                                35

SEQ ID NO: 6               moltype = DNA  length = 29
FEATURE                    Location/Qualifiers
source                     1..29
                           mol_type = other DNA
                           organism = synthetic construct
SEQUENCE: 6
tcctgcatgc actagtgcta gcgtcaaat                                       29

SEQ ID NO: 7               moltype = DNA  length = 31
FEATURE                    Location/Qualifiers
source                     1..31
                           mol_type = other DNA
                           organism = synthetic construct
SEQUENCE: 7
tagcactagt gcatgcagga atctctggca c                                    31

SEQ ID NO: 8               moltype = DNA  length = 35
FEATURE                    Location/Qualifiers
source                     1..35
                           mol_type = other DNA
                           organism = synthetic construct
SEQUENCE: 8
gacaggacat tgtgaatatc aagaattgta tgaac                                35

SEQ ID NO: 9               moltype = DNA  length = 30
FEATURE                    Location/Qualifiers
source                     1..30
                           mol_type = other DNA
                           organism = synthetic construct
SEQUENCE: 9
gatattcaca atgtcctgtc caacttctgc                                      30

SEQ ID NO: 10              moltype = DNA  length = 48
FEATURE                    Location/Qualifiers
source                     1..48
                           mol_type = other DNA
                           organism = synthetic construct
```

```
SEQUENCE: 10
ggcggccgcc gcggctcgag gtaccttact atctgtgttg agtcctgg                    48

SEQ ID NO: 11           moltype = DNA   length = 35
FEATURE                 Location/Qualifiers
source                  1..35
                        mol_type = other DNA
                        organism = synthetic construct
SEQUENCE: 11
tcgaaacgag gaattatggc catgaacgaa aacgg                                   35

SEQ ID NO: 12           moltype = DNA   length = 37
FEATURE                 Location/Qualifiers
source                  1..37
                        mol_type = other DNA
                        organism = synthetic construct
SEQUENCE: 12
tgggccacgt gaattctatt aggcgatacc aaccttg                                 37

SEQ ID NO: 13           moltype = DNA   length = 35
FEATURE                 Location/Qualifiers
source                  1..35
                        mol_type = other DNA
                        organism = synthetic construct
SEQUENCE: 13
tcgaaacgag gaattatgtc ctgtccaact tctgc                                   35

SEQ ID NO: 14           moltype = DNA   length = 38
FEATURE                 Location/Qualifiers
source                  1..38
                        mol_type = other DNA
                        organism = synthetic construct
SEQUENCE: 14
tgggccacgt gaattttact atctgtgttg agtcctgg                                38

SEQ ID NO: 15           moltype = DNA   length = 39
FEATURE                 Location/Qualifiers
source                  1..39
                        mol_type = other DNA
                        organism = synthetic construct
SEQUENCE: 15
caaaacacag gcgcgatgac aatgcctcat cgctatatg                               39

SEQ ID NO: 16           moltype = DNA   length = 40
FEATURE                 Location/Qualifiers
source                  1..40
                        mol_type = other DNA
                        organism = synthetic construct
SEQUENCE: 16
ttaaacagtg gcgcgttaaa taattgccag caataaggac                              40

SEQ ID NO: 17           moltype = DNA   length = 39
FEATURE                 Location/Qualifiers
source                  1..39
                        mol_type = other DNA
                        organism = synthetic construct
SEQUENCE: 17
acatcaaaag gcgcgatgac aatgcctcat cgctatatg                               39

SEQ ID NO: 18           moltype = DNA   length = 40
FEATURE                 Location/Qualifiers
source                  1..40
                        mol_type = other DNA
                        organism = synthetic construct
SEQUENCE: 18
ttaaacagtg gcgcgttaaa taattgccag caataaggac                              40
```